United States Patent
Kiesel et al.

(10) Patent No.: US 7,633,629 B2
(45) Date of Patent: Dec. 15, 2009

(54) TUNING OPTICAL CAVITIES

(75) Inventors: Peter Kiesel, Palo Alto, CA (US); Oliver Schmidt, Palo Alto, CA (US); Michael Bassler, Menlo Park, CA (US); Uma Srinivasan, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 142 days.

(21) Appl. No.: 11/702,321

(22) Filed: Feb. 5, 2007

(65) Prior Publication Data

US 2008/0186508 A1    Aug. 7, 2008

(51) Int. Cl.
*G01B 9/02* (2006.01)
(52) U.S. Cl. .......................... 356/519; 356/517
(58) Field of Classification Search ................. 356/454, 356/519, 480, 517
See application file for complete search history.

(56) References Cited

U.S. PATENT DOCUMENTS

| | | | |
|---|---|---|---|
| 4,455,089 A | 6/1984 | Yeung et al. | |
| 4,820,042 A | 4/1989 | Barger | |
| 5,144,498 A | 9/1992 | Vincent | |
| 5,243,614 A | 9/1993 | Wakata et al. | |
| 5,461,477 A | 10/1995 | Marinelli et al. | |
| 5,666,195 A | 9/1997 | Shultz et al. | |
| 5,760,900 A | 6/1998 | Ito et al. | |
| 5,784,507 A | 7/1998 | Holm-Kennedy et al. | |
| 6,049,727 A | 4/2000 | Crothall | |
| 6,216,022 B1 | 4/2001 | Tyrrell et al. | |
| 6,285,504 B1 | 9/2001 | Diemeer | |
| 6,295,130 B1 | 9/2001 | Sun et al. | |
| 6,519,074 B2 | 2/2003 | Little et al. | |
| 6,529,659 B2 | 3/2003 | Little et al. | |

(Continued)

FOREIGN PATENT DOCUMENTS

WO    WO 95/20144    7/1995

(Continued)

OTHER PUBLICATIONS

Liang, X.J., Liu, A.Q., Zhang, X.M., Yap, P.H., Ayi, T.C., Yoon, H.S., "Refractive Index Measurement of Single Living Cell Using a Biophotonic Chip for Cancer Diagnosis Applications," 9th International Conference on Miniaturized Systems for Chemistry and Life Sciences, Oct. 9-13, 2005, 3 pages.

(Continued)

*Primary Examiner*—Hwa (Andrew) S Lee
(74) *Attorney, Agent, or Firm*—Leading-Edge Law Group, PLC; James T. Beran

(57) ABSTRACT

A tunable optical cavity can be tuned by relative movement between two reflection surfaces, such as by deforming elastomer spacers connected between mirrors or other light-reflective components that include the reflection surfaces. The optical cavity structure includes an analyte region in its light-transmissive region, and presence of analyte in the analyte region affects output light when the optical cavity is tuned to a set of positions. Electrodes that cause deformation of the spacers can also be used to capacitively sense the distance between them. Control circuitry that provides tuning signals can cause continuous movement across a range of positions, allowing continuous photosensing of analyte-affected output light by a detector.

30 Claims, 10 Drawing Sheets

U.S. PATENT DOCUMENTS

| | | | |
|---|---|---|---|
| 6,580,507 | B2 | 6/2003 | Fry et al. |
| 6,594,022 | B1 | 7/2003 | Watterson et al. |
| 6,597,461 | B1 * | 7/2003 | Verma et al. ............... 356/519 |
| 6,639,679 | B2 | 10/2003 | Frojdh |
| 6,665,109 | B2 | 12/2003 | Little et al. |
| 6,717,965 | B2 | 4/2004 | Hopkins, II et al. |
| 6,747,775 | B2 | 6/2004 | Little |
| 6,747,784 | B2 | 6/2004 | Little et al. |
| 6,809,865 | B2 | 10/2004 | Chen |
| 6,822,798 | B2 * | 11/2004 | Wu et al. ................... 359/578 |
| 6,865,198 | B2 | 3/2005 | Taubman |
| 6,867,868 | B1 | 3/2005 | Barbarossa |
| 6,952,603 | B2 | 10/2005 | Gerber et al. |
| 7,064,836 | B2 | 6/2006 | Bechtel et al. |
| 7,149,396 | B2 | 12/2006 | Schmidt et al. |
| 7,291,824 | B2 | 11/2007 | Kiesel et al. |
| 7,310,153 | B2 | 12/2007 | Kiesel et al. |
| 7,315,667 | B2 | 1/2008 | Schmidt et al. |
| 7,358,476 | B2 | 4/2008 | Kiesel et al. |
| 7,466,409 | B2 | 12/2008 | Scherer et al. |
| 7,471,399 | B2 | 12/2008 | Kiesel et al. |
| 7,479,625 | B2 | 1/2009 | Kiesel et al. |
| 7,502,123 | B2 | 3/2009 | Kiesel et al. |
| 7,522,786 | B2 | 4/2009 | Kiesel et al. |
| 7,545,513 | B2 | 6/2009 | Kiesel et al. |
| 7,547,904 | B2 | 6/2009 | Schmidt et al. |
| 7,554,673 | B2 | 6/2009 | Kiesel et al. |
| 2003/0191377 | A1 | 10/2003 | Robinson et al. |
| 2003/0235924 | A1 | 12/2003 | Adams et al. |
| 2005/0164320 | A1 | 7/2005 | McDevitt et al. |
| 2006/0039009 | A1 | 2/2006 | Kiesel et al. |
| 2006/0181710 | A1 | 8/2006 | Kachanov et al. |
| 2006/0182659 | A1 * | 8/2006 | Unlu et al. ............... 422/82.05 |
| 2007/0070347 | A1 | 3/2007 | Scherer et al. |
| 2007/0076210 | A1 | 4/2007 | Kiesel et al. |
| 2007/0147726 | A1 | 6/2007 | Kiesel et al. |
| 2007/0148760 | A1 | 6/2007 | Kiesel et al. |
| 2008/0128595 | A1 | 6/2008 | Kiesel et al. |
| 2008/0186483 | A1 | 8/2008 | Kiesel et al. |
| 2008/0186488 | A1 | 8/2008 | Kiesel et al. |
| 2008/0186492 | A1 | 8/2008 | Kiesel et al. |
| 2008/0186494 | A1 | 8/2008 | Kiesel et al. |
| 2008/0186500 | A1 | 8/2008 | Schmidt et al. |
| 2008/0186503 | A1 | 8/2008 | Kiesel et al. |
| 2008/0186504 | A1 | 8/2008 | Kiesel et al. |
| 2008/0187011 | A1 | 8/2008 | Kiesel et al. |
| 2008/0197272 | A1 | 8/2008 | Kiesel et al. |

FOREIGN PATENT DOCUMENTS

| | | | |
|---|---|---|---|
| WO | 2006013360 | A2 | 12/2006 |

OTHER PUBLICATIONS

Kondziela, J., "Accurately Measure Laser Spectral Chracteristics," www.exfo.com, 2006, 5 pages.

Vogel, W., Berroth, M., "Tuneable liquid crystal Fabry-Perot filters", Institute for Electrical and Optical Communication Engineering, University of Stuttgart, 2002, 10 pages.

Spear, J.D., Russo, R.E., "Low noise position sensitive detector for optical probe beam deflection measurements," REv. Sci. Instrum. 67 (7), Jul. 1996, pp. 2481-2484.

PSI Corp., Adaptive InfraRed Imaging Spectroradiometry AIRIS, 10 pp, printed from www.psicorp.com on Jan. 26, 2007.

JDS Unipase Corp., "Linear Variable Filters," 8 pp., printed from gallary.bcentral.com on Jan. 28, 2007.

Shah, M. A., Shanmugan, V., Chowdhury, G. K., and Akkipeddi, R., "Optomechanical design of tunable InP-based Fabry-Perot filters for wavelength division multiplexing applications," J. Microlith., Microfab., Microsyst., vol. 4, Oct.-Dec. 2005, pp. 041303-1 to 041303-8.

Office communication in U.S. Appl. No. 11/702,249, mailed Aug. 7, 2008, 16 pages, published in PAIR.

Amendment in U.S. Appl. No. 11/702,249, submitted Nov. 7, 2008, 30 pages, published in PAIR.

Notice of Allowance and Fee(s) Due in U.S. Appl. No. 11/702,249, mailed Nov. 28, 2008, 9 pages, published in PAIR.

Amendment in U.S. Appl. No. 11/702,470, submitted Jul. 25, 2008, 21 pages, published in PAIR.

Office communication in U.S. Appl. No. 11/702,470, mailed Oct. 31, 2008, 22 pages, published in PAIR.

Office communication in U.S. Appl. No. 11/702,363, mailed Sep. 4, 2008, 29 pages, published in PAIR.

Office communication in U.S. Appl. No. 11/702,325, mailed Aug. 15, 2008, 14 pages, published in PAIR.

Amendment in U.S. Appl. No. 11/702,325, submitted Nov. 17, 2008, 38 pages, published in PAIR.

Office communication in U.S. Appl. No. 11/702,470, mailed Apr. 25, 2008, 22 pages, published in PAIR.

Amendment in U.S. Appl. No. 11/702,470, submitted Jan. 30, 2009, 22 pages, published in PAIR.

Notice of Allowance and Fee(s) Due in U.S. Appl. No. 11/702,470, mailed Apr. 24, 2009, 15 pages, published in PAIR.

Amendment with Information Disclosure in U.S. Appl. No. 11/702,363, submitted Dec. 4, 2008, 34 pages, published in PAIR.

Notice of Allowance and Fee(s) Due in U.S. Appl. No. 11/702,363, mailed Mar. 23, 2009, 12 pages, published in PAIR.

Office communication in U.S. Appl. No. 11/702,325, mailed Feb. 10, 2009, 8 pages, published in PAIR.

Response with Terminal Disclaimer in U.S. Appl. No. 11/702,325, submitted May 5, 2009, 5 pages, published in PAIR.

Office communication in U.S. Appl. No. 11/702,320, mailed Apr. 16, 2009, 9 pages, published in PAIR.

Amendment in U.S. Appl. No. 11/702,320, submitted May 7, 2009, 29 pages, published in PAIR.

Office communication in U.S. Appl. No. 11/702,328, mailed May 27, 2009, 28 pages, published in PAIR.

* cited by examiner

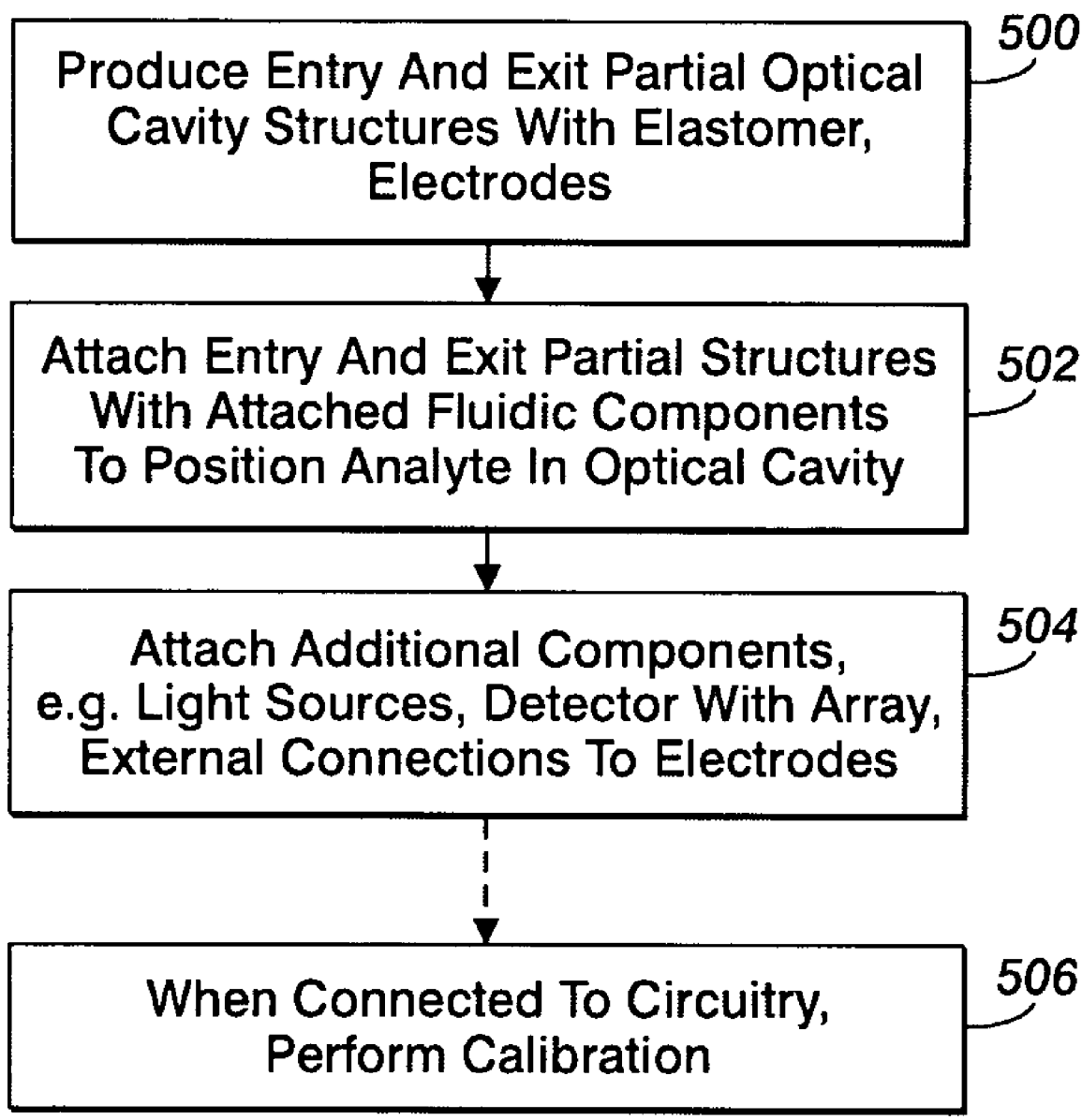

TUNING OPTICAL CAVITIES

This application is related to the following co-pending applications, each of which is hereby incorporated by reference in its entirety: "Chip-Size Wavelength Detector", U.S. patent application Ser. No. 10/922,870, now published as U.S. Patent Application Publication No. 2006/0039009; "Sensing Photon Energies Emanating From Channels or Moving Objects", U.S. patent application Ser. No. 11/315, 992; "Photosensing Throughout Energy Range and in Subranges", U.S. patent application Ser. No. 11/316,438; "Position-Based Response to Light", U.S. patent application Ser. No. 11/316,302; "Photosensing Optical Cavity Output Light", U.S. patent application Ser. No. 11/702,250; "Encoding Optical Cavity Output Light", U.S. patent application Ser. No. 11/702,363; "Obtaining Information From Optical Cavity Output Light", U.S. patent application Ser. No. 11/702, 249; "Distinguishing Objects", U.S. patent application Ser. No. 11/702,328; "Implanting Optical Cavity Structures", U.S. patent application Ser. No. 11/702,329; "Containing Analyte In Optical Cavity Structures", U.S. patent application Ser. No. 11/702,325; and "Tuning Optical Cavities", U.S. patent application Ser. No. 11/702,320.

BACKGROUND OF THE INVENTION

The present invention relates generally to techniques involving tuning of optical cavities, such as cavities whose output light can include information, such as about analytes.

Various optical cavities have been proposed that have features related to tuning. U.S. Pat. Nos. 6,295,130 and 6,597, 461, for example, describe two different types of tunable Fabry-Perot cavities. U.S. Pat. No. 6,285,504 describes a variable optical filter in which the optical path length of a resonant cavity between partially reflective surfaces can be varied. U.S. Pat. No. 6,747,775 describes a detunable Fabry-Perot interferometer.

It would be advantageous to have improved techniques for tuning optical cavities.

SUMMARY OF THE INVENTION

The invention provides various exemplary embodiments, including products, systems, methods, apparatus, and devices. In general, the embodiments involve optical cavities that can be tuned and that include regions in which analyte can be present.

These and other features and advantages of exemplary embodiments of the invention are described below with reference to the accompanying drawings.

BRIEF DESCRIPTION OF THE DRAWINGS

FIG. 14 is a flowchart showing operations in producing devices as in FIGS. 10 and 11.

DETAILED DESCRIPTION

Figure 1:
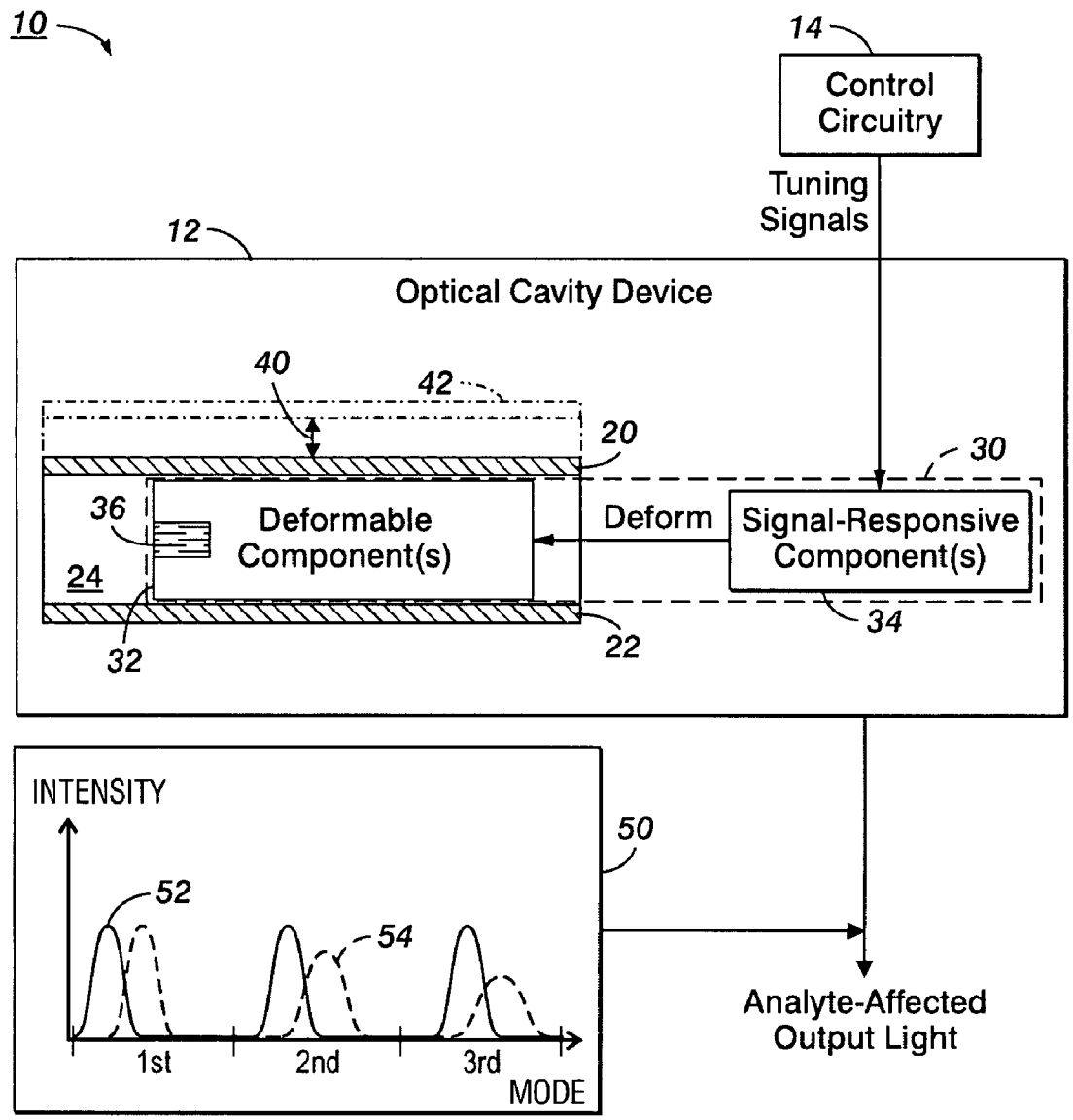
FIG. 1 is a schematic diagram of a system in which an optical cavity device includes a tunable optical cavity that can contain analyte.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum.

The term "photon" refers herein to a quantum of light, and the term "photon energy" refers herein to the energy of a photon. Light can be described as having a "photon energy distribution", meaning the combination of photon energies that are included in the light; highly monochromatic light, for example, has a photon energy distribution with one peak energy value. A photon energy distribution can be specified in space and time: For example, a photon energy distribution can be specified as a function of position, such as on a surface, or as a function of time; a photon energy distribution that is "homogeneous" is substantially the same at all relevant positions, such as the positions of a surface, while a photon energy distribution that is "stable" is substantially the same at all relevant times.

Light can also be described as provided by a "light source," which, unless otherwise specified, refers herein to any device, component, or structure that can provide light of the type described; examples of light sources relevant to the below-described implementations include various kinds of pulsed and unpulsed lasers and laser structures, light emitting diodes (LEDs), superluminescent LEDs (SLEDs), resonant cavity LEDs, sources of broadband light that is spectrally filtered such as with a monochromator, and so forth. A "tunable light source" is a light source that provides light with a predominant photon energy that can be changed in response to a signal or operation of some kind.

The term "laser" is used herein to mean any region, element, component, or device in which transitions between energy levels can be stimulated to cause emission of coherent light, such as in the ultraviolet, visible, or infrared regions of the spectrum. A "laser structure" is any structure that includes one or more lasers. A "laser cavity" is a region of a laser in which transitions can be stimulated to cause emission.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where light changes direction in a way that can be illustrated as a vertex between an incoming ray and an outgoing ray, the change may be referred to as a "reflection"; similarly, to "reflect" light is to cause the light to change its direction of propagation approximately at a surface, referred to herein as a "reflection surface". Where light propagates at less than c, it may be useful to obtain an "optical distance" of propagation; for any segment of length d in which speed of propagation is constant $\in$*c, where $\in \leq 1$, optical distance $D(\in)=d/\in$. An optical distance may be referred to herein as an "optical thickness", such as where light is propagating through a thickness of material.

To "photosense" is to sense photons, and to "photosense quantity" of photons is to obtain information indicating a quantity of the photons. Photons that are photosensed are sometimes referred to herein as "incident photons". A surface at which photosensing occurs is referred to herein as a "photosensitive surface".

A "photosensor" is used herein to refer generally to any element or combination of elements that senses photons, whether by photosensing quantity or any other information about the photons. A photosensor could, for example, provide an electrical signal or other signal that indicates results of sensing, such as a signal indicating quantity of incident photons; in general, signals from a photosensor that indicate results of sensing are referred to herein as "sensing results". If electrical sensing events occur in a photosensor in response to incident photons, the photosensor may integrate or otherwise accumulate the results of the electrical sensing events during a time period referred to herein as a "sensing period" or "sense period".

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described. A central wavelength or frequency or other value indicating a central photon energy of a range or subrange is sometimes referred to herein as a "central energy", and may be obtained in various ways, such as by finding an energy that has maximum intensity or that is another type of central value such as a mean or median of the distribution of light within the range or subrange.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry.

Circuitry can be described based on its operation or other characteristics. For example, circuitry that performs control operations is sometimes referred to herein as "control circuitry"; and circuitry that performs processing operations is sometimes referred to herein as "processing circuitry".

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations of ICs described herein include features characterized as "cells" (or "elements") and "arrays", terms that are used with related meanings: An "array" is an arrangement of "cells" or "elements"; unless otherwise indicated by the context, such as for a biological cell, the words "cell" and "element" are used interchangeably herein to mean a cell or an element of an array. An array may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

Some of the implementations below are described in terms of "rows" and "columns", but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

An IC includes a "photosensor array" if the IC includes an array of cells, and at least some of the cells include respective photosensors. A cell that includes a photosensor may also include "cell circuitry", such as circuitry that makes connections with the photosensor, that transfers signals to or from the photosensor, or that performs any other operation other than photosensing. In general, a cell's photosensor and cell circuitry are within a bounded area of the array, an area sometimes referred to herein as the "cell's area". The part of a cell's area in which an incident photon can be photosensed is referred to herein as "sensing area".

In an application of an IC that includes a photosensor array, circuitry that "responds to" one or more photosensors can be any circuitry that, in operation, receives information from the photosensors about their photosensing results through an electrical connection. Circuitry that responds to a photosensor could be circuitry in the same cell as the photosensor, or it could be array circuitry, peripheral circuitry, or other external circuitry, or it could include any suitable combination of cell circuitry, array circuitry, peripheral circuitry, and other external circuitry. Circuitry that responds to a photosensor could employ any suitable technique to read out photosensing results, including, for example, CCD, CMOS, or photodetector array (PDA) techniques.

An IC is or includes a "position-sensitive detector" or "PSD" if it includes a substantially continuous photosensitive surface and it provides electrical signals indicating a position resulting from a pattern of incident light on the photosensitive surface. For example, the signals could be two currents whose normalized difference is proportional to a centroid of the incident light pattern.

FIG. 1 illustrates general features of system 10, an example of a system that can be implemented as described in greater detail below. As with other implementations described below, system 10 involves a combination of parts or components. As used herein, a "system" is a combination of two or more parts or components that can perform an operation together. A system may be characterized by its operation: for example, an "analyte information system" is a system that operates somehow on analyte information; a "processing system" is a system that performs data or signal processing; and so forth.

Within a system, components and parts may be referred to in a similar manner. One component of an analyte information system in which information is obtained about an analyte's optical characteristics, for example, can be a "detector component" or simply "detector", meaning a component that detects light; similarly, a "light source component" includes one or more light sources; an "optical component" performs an optical operation; a "photosensing component" performs a photosensing operation; a "deformable component" that can be changed in shape in response to stress or other internal or external forces, some examples of which are described below; a "signal-responsive component"; an "electrode component" or simply "electrode", meaning an electrically conductive part that is connected to a current path and is of the sort that operates in relation to one or more other electrode, such as by controlling an electrostatic field between the electrodes or by establishing electrical contact to a component that is between electrodes in a circuit; a "sensing component" that can sense an item, e.g. a shape of a deformable component; a "light-transmissive component" or simply "transmission component" transmits light; a "light-reflective component" or simply "reflective component" reflects light; and other examples are defined further below. Other parts or components can be characterized by their structure.

In the implementations described below, structures, systems, or parts or components of structures or systems may sometimes be referred to as "attached" to each other or to other structures, systems, parts, or components or visa versa, and operations are performed that "attach" structures, systems, or parts or components of structures or systems to each other or to other things or visa versa; the terms "attached", "attach", and related terms refer to any type of connecting that could be performed in the context. One type of attaching is "mounting", which occurs when a first part or component is attached to a second part or component that functions as a support for the first. In contrast, the more generic term "connecting" includes not only "attaching" and "mounting", but also making other types of connections such as electrical connections between or among devices or components of circuitry. A combination of one or more parts connected in any way is sometimes referred to herein as a "structure".

A structure may be described by its operation, such as a "support structure" that can operate as a support as described above; similarly, an "optical cavity structure" includes parts or components that can operate as an optical cavity; a "tuning structure" that can perform a tuning operation; other examples are defined below. In addition, a structure may be characterized by the nature of its parts or the way in which they are connected; for example, a "layered structure" is a structure that includes one or more layers, and a "partial structure" refers to a structure that is in turn part of another structure.

System 10 includes device 12 and control circuitry 14. Device 12 in turn includes light-reflective components 20 and 22 and, between them, light-transmissive region 24 into which components 20 and 22 reflect light, so that light-transmissive region is between two inward reflection regions provided by components 20 and 22. Device 12 also includes tuning structure 30, a structure than can respond to tuning signals, illustratively from control circuitry 14, by moving light-reflective components 20 and 22 relative to each other, which has the effect of tuning optical cavity operation by moving its inward reflection surfaces relative to each other. As used herein, an optical cavity's operation, or the optical cavity itself, is "tuned" when it is changed in some way, such as by changing the shape of its light-transmissive region so that it transmits a different wavelength range.

Tuning structure 30 illustratively includes one or more elastically deformable components 32 and one or more signal-responsive components 34, although tuning could be performed in many other ways, with or without deformable components. Deformable components 32 could optionally each be an "elastically deformable component", meaning a deformable component of any kind that can return at least approximately to a previous shape after deformation; as used herein, elastically deformable components could be, but need not be, spring-like, and an elastically deformable component could require at least some force to return it to its previous shape, which would also be treated as a deformation; but in some implementations with only a single adjustment, elasticity would not be required. Also, the term "shape" is used herein to encompass size, so that a deformable component (whether or not elastic), in addition to being deformed by forces that change the category or proportions of its shape, is also considered deformed by a force that changes only its size; therefore, a deforming force could allow a deformable component to retain a shape of the same category, such as a cylinder or cube, with all its dimensions similarly scaled as it changes size, as can occur, for example, with some inflatable components.

Signal-responsive components 34 receive tuning signals, and, in response, cause deformation of deformable components 32, such as electrostatically, electromagnetically, magnetically, piezoelectrically, thermally, or mechanically. Deformable components 32 are connected so that deformation caused by signal-responsive components 34 in turn causes light-reflective components 20 and 22 to move relative to each other, changing the optical cavity's shape; for example, either of light-reflective components 20 and 22 could move while the other remains at a fixed position or both could move, such as relative to a support structure. Deformable components 32 can be at least partially within light-transmissive region 24 as shown or can have surface area that bounds or extends into light-transmissive region 24, but within light-transmissive region 24 there is also an analyte region 36 in which analyte can be present, illustratively an opening defined in and bounded by deformable components 32 (and there could also be a reference region containing a reference fluid or the like). Presence of analyte in region 30 affects the cavity's output light when the cavity's operation is tuned to certain relative positions of the inward reflection surfaces, referred to as a "set of relative positions". A set of relative positions can include a "range of relative positions", referring to a substantially continuous subset of the set.

Bidirectional arrows 40 illustrate a range of positions through which light-reflective component 20 can move relative to light-reflective component 22 in response to deformation of components 32, with another position of light-reflective component 20 being illustrated by dashed outline 42. Therefore, operation of signal-responsive components 34 causes light-reflective components 20 and 22 to move relative to each other within the range of positions indicated by arrows 40. The range includes a subrange of one or more positions in which components 20 and 22 and light-transmissive region 24, with analyte in analyte region 36, can operate as an optical cavity that provides output light. The output light can include information about optical characteristics of the analyte.

The term "reflective optical cavity", or simply "optical cavity" or "cavity", refers herein to a light-transmissive region that is at least partially bounded by light-reflective components, with the light-reflective components and the light-transmissive region having characteristics such that a measurable portion of light within the light-transmissive region is reflected more than once across the light-transmissive region. An "optical cavity component" or "optical cavity device" is a component or device, respectively, that includes one or more optical cavities.

Within the broad category of optical cavities, there are various more specific types: For example, a laser cavity, mentioned above, is an example of an "emitting optical cavity" or simply "emitting cavity" that can operate as a source of emitted output light even when it is not receiving input light from an external light source, with the emitted light ordinarily resulting from a gain medium within the light-transmissive region; similarly, a "transmissive cavity" can operate, in response to input light from one or more external light sources at an entry surface, providing a transmitted portion of its output light at an exit surface different than the entry surface (a complementary, reflected portion may be provided at the entry surface); a "Fabry-Perot cavity" is a reflective optical cavity in which constructive interference (or positive reinforcement) occurs in one or more photon energy subranges while destructive interference occurs in others.

A Fabry-Perot cavity or other optical cavity that can operate to provide output light in one or more photon energy subranges while not providing output light with other photon energies may be described as having one or more "modes", each for a respective one of the output light energy subranges; if the cavity is a transmissive cavity, modes of its transmitted output light may be referred to as "transmission modes" and modes of its reflected output light may be referred to as "reflection modes". In the reflection spectrum, either the valley-like dips or the plateau-like reflection bands between the dips can be considered a "reflection modes". An emitting cavity can be described as "stimulated at" a mode by any operation that results in emission of output light in the mode's photon energy subrange. Similarly, a transmissive cavity can be described as "illuminated at" a mode by any operation that provides input light that results in transmission or reflection of output light in the mode's photon energy subrange.

In typical implementations of optical cavities, two light-reflective components have approximately parallel reflection surfaces and the light-transmissive region is sufficiently uniform that measurements would indicate many reflections of light within the light-transmissive region. Such cavities define a directional orientation as follows: Directions in which light could propagate and be reflected many times within the light-transmissive region are referred to herein as "reflection directions", and generally include a range of directions that are approximately perpendicular to both reflection surfaces. Directions that are approximately parallel to both reflection surfaces, on the other hand, are generally referred to herein as "lateral directions". In addition, the terms "in", "inward", or "internal" generally refer to positions, directions, and other items within or toward the light-transmissive region between the reflection surfaces, while "out", "outward", and "external" refer to positions, directions, and other items outside or away from the light-transmissive region. In general, it should be understood that the above directional orientation is arbitrary and only for ease of description, and that an optical cavity may have any appropriate orientation.

The above directional orientation does not in general apply to angle of incidence of input light. Transmissive cavities can typically operate in response to incident light that is not perpendicular to entry surfaces or reflection surfaces. Light incident on a transmissive cavity's entry surface at any angle is reflected multiple times within the cavity, producing transmission modes in accordance with the cavity's geometry. But transmission modes are affected by angle of incidence:

Depending on the type of cavity and the angle of incidence, modes can be blue shifted or red shifted in comparison to perpendicular incidence; if all light enters a cavity at approximately the same angle, performance is affected only by the shifting of modes and modes are not also broadened, but performance is reduced if a cavity receives incident light distributed across a large angular range because transmission mode structure is then averaged over multiple angles.

Analyte is "present in", "positioned in", "contained in", or simply "in" an optical cavity when the analyte is in all or some part of the cavity's light-transmissive region; the optical cavity may be said to "contain" the analyte or to be an "analyte-containing optical cavity". An optical cavity provides "analyte-affected output light" if the optical cavity's output light is different in some way when analyte is present in the cavity than when analyte is absent, with the difference being due to the analyte's optical characteristics.

More generally, a cavity "includes a region" if the region is all or some part of the cavity's light-transmissive region. An "analyte region", therefore, is a region that can contain analyte.

The various exemplary implementations described below address problems that arise in obtaining information from output light of tunable optical cavities, such as information about analytes. The implementations are especially relevant to output light that includes information about an analyte's optical characteristics. One problem is that previous techniques provide limited flexibility in how a tunable optical cavity's output light is affected by the analyte's optical characteristics, in part because certain cavity features are fixed or inflexible. Another is that some techniques rely on complex and expensive ways to manufacture, use, or tune cavities.

As shown in FIG. 1, during optical cavity operation with analyte in region 36, device 12 provides analyte-affected output light. The graph in box 50 illustrates examples of analyte-affected output light that could be provided if the optical cavity provides output light in modes. The graph shows an "intensity function" for each of three modes, meaning that intensity of output light from each mode can be represented as a function of another parameter, such as of photon energy or, in some implementations, of position.

An intensity function can have any of a wide variety of shapes and features, but a shape that frequently arises in transmission modes is the "peak", a shape characterized by a maximum value from which a curve for the function slopes steeply downward. Peaks have various features, including "central value", meaning the value of the other parameter at which the peak's maximum occurs, such as "central energy" for an intensity-energy function; "maximum intensity" or simply "maximum" or "amplitude", meaning the intensity value at the peak's maximum, whether measured as an absolute intensity or relative to another feature, such as a nearby minimum value; "contrast", meaning a value indicating relationship between magnitudes of the peak's maximum intensity and of one or more nearby minima of the transmission intensity function; and "intermediate intensity width", meaning the width of the peak at an intensity somewhere between its maximum and nearby minima, such as a full width half maximum (FWHM). In general, information can be encoded in one of these features in various ways, including those described in co-pending U.S. patent application Ser. No. 11/702,363, entitled "Encoding Optical Cavity Output Light" and incorporated herein by reference in its entirety. Once encoded, such information can also be recovered in various ways, including those described in co-pending U.S. patent application Ser. No. 11/702,249, entitled "Obtaining Information From Optical Cavity Output Light" and incorporated herein by reference in its entirety.

Information about an optical characteristic of analyte in analyte region 36 can be encoded in a mode's intensity function, such as by changing its central energy or changing its amplitude, its contrast, or its FWHM (or other intermediate intensity width). Some such changes are shown in the graph as differences between solid-line curve 52 and dashed-line curve 54: Central energies of the intensity functions for the first, second and third modes are illustratively shifted from curve 52 to curve 54, such as by a change in refractive index; similarly, amplitudes, contrasts, and FWHMs of the intensity functions of the second and third modes are changed from curve 52 to curve 54, such as by changes in absorption spectrum. Curve 52 might be obtained, for example, with analyte absent, while curve 54 might be obtained with analyte present, changing refractive index and absorption spectrum of the optical cavity. Additional details about effects of refractive index and absorption and encoding techniques are provided in co-pending U.S. patent application Ser. No. 11/702,363, entitled "Encoding Optical Cavity Output Light" and incorporated herein by reference in its entirety. Additional details about ways in which information can be obtained from analyte-affected output light from inhomogeneous cavities are provided in co-pending U.S. patent application Ser. No. 11/702,325, entitled "Containing Analyte In Optical Cavity Structures" and incorporated herein by reference in its entirety.

The general features in FIG. 1 could be implemented in many ways, as exemplified by the various implementations described below. In particular, the exemplary implementations below include examples of how control circuitry could control tuning structures by providing signals to signal-responsive components, and many other types of control circuitry, signal-responsive components, and control techniques could be employed.

Many different types of mirrors and other light-reflective components could be used in an optical cavity device, some of which are described below. Also, elastomer spacers and various other kinds of deformable components could be used in optical cavity tuning, some examples of which are described below. Further, spacers or other deformable components could be connected to cause mirror movement in any of a wide variety of ways. For example, they could be connected as a result of a fabrication technique in which spacers are formed as by photolithography on the mirrors. Furthermore, various bonding, adhesive, or similar techniques could be used to make a similar connection between them.

To also provide an analyte region between mirrors, an opening can be provided in one or more elastically deformable components as shown in FIG. 1; the light-transmissive region can include, in addition to all or part of the elastically deformable components, a structure that operates as a channel, a duct, a well, or other component that can contain analyte, which may be especially useful with fluid analytes such as liquid, gas, or aerosol or fluid-borne analytes such as in biological cells; the light-transmissive region can be open, such as between spacers as described below, which may be especially suitable for monitoring gases or airborne analytes or, more generally, for an air-spaced cavity; or elastically deformable components can be positioned around but outside the light-transmissive region, connected, for example, to parts of light-reflective components 20 and 22 outside light-transmissive region 24, while the analyte region includes all or some part of the light-transmissive region, with or without enclosure.

Figure 2:
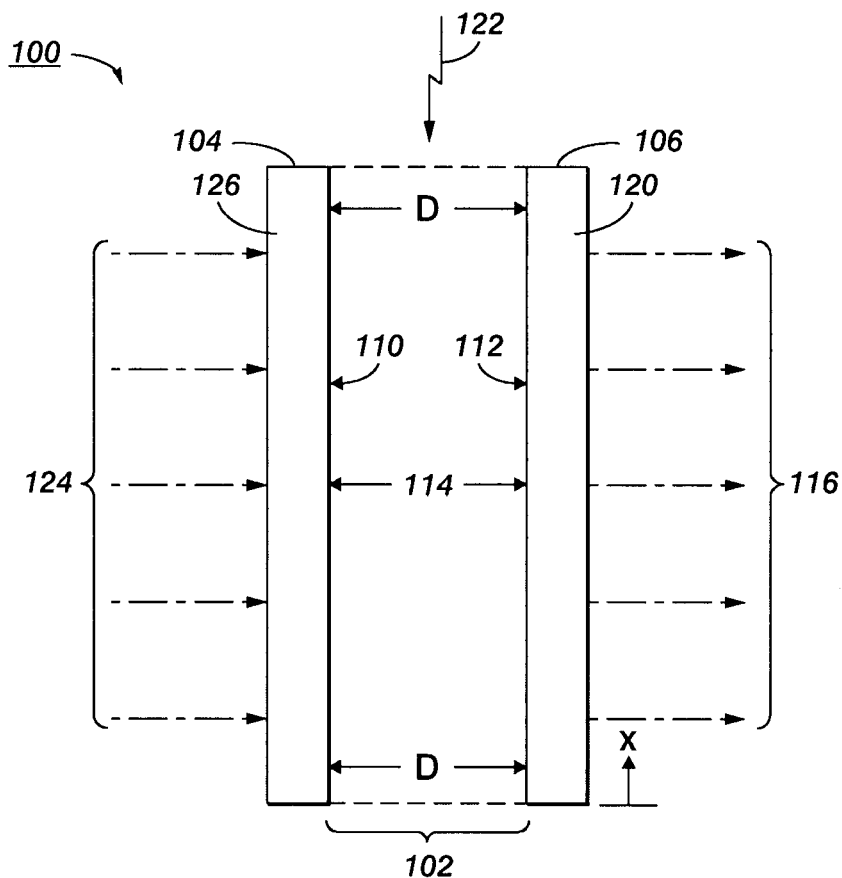
FIG. 2 is a schematic side view of a homogeneous optical cavity that could be used in the system of FIG. 1.

FIG. 2 illustrates optical cavity 100, an example of a "homogeneous optical cavity", meaning a cavity whose light-transmissive region includes an extended part with substantially constant optical distance D between its reflection surfaces, sometimes referred to as its "homogeneous region". The homogeneous region of cavity 100 illustratively includes substantially all of light-transmissive region 102 where it is between and partially bounded by light-reflective components 104 and 106, though partially and completely bounded homogeneous regions with various other shapes and arrangements are possible.

Inward-facing surfaces 110 and 112 of components 104 and 106, respectively, can be implemented, for example, as mirrors or other reflective components that closely approximate the reflection surfaces of cavity 100. The characteristics of components 104 and 106 and of any material or structure within region 102 are such that a measurement would indicate that at least a portion of light within region 102 is reflected more than once. A reflection direction in which light can be repeatedly reflected between the reflection surfaces is represented by bidirectional ray 114, while one of the possible lateral directions in an x-y plane approximately perpendicular to ray 114 is illustrated by an x-axis at the lower right.

FIG. 2 also illustrates two ways in which homogeneous optical cavities can operate to provide output light, represented schematically by arrows 116. In both operations, output light can be provided at an exit surface, illustratively outward-facing surface 120 of component 106, which may or may not be approximately parallel to the reflection surfaces.

In the first operation, optical cavity 100 operates as an emitting cavity, such as a laser cavity. Typically, an emitting cavity operates in response to stimulation of some type, represented schematically in FIG. 2 by stimulation arrow 122. Stimulation arrow 122 could, for example, represent electrical or optical stimulation.

In the second operation, optical cavity 100 operates as a transmissive cavity, such as a Fabry-Perot interferometer. A transmissive cavity operates in response to input light from one or more external light sources, represented in FIG. 2 by illumination arrows 124. Input light can be received at an entry surface, illustratively outward-facing surface 126 of component 104, which also may or may not be approximately parallel to the reflection surfaces. As noted above, a reflected portion of output light can be provided at the entry surface, as described in greater detail below.

Figure 3:
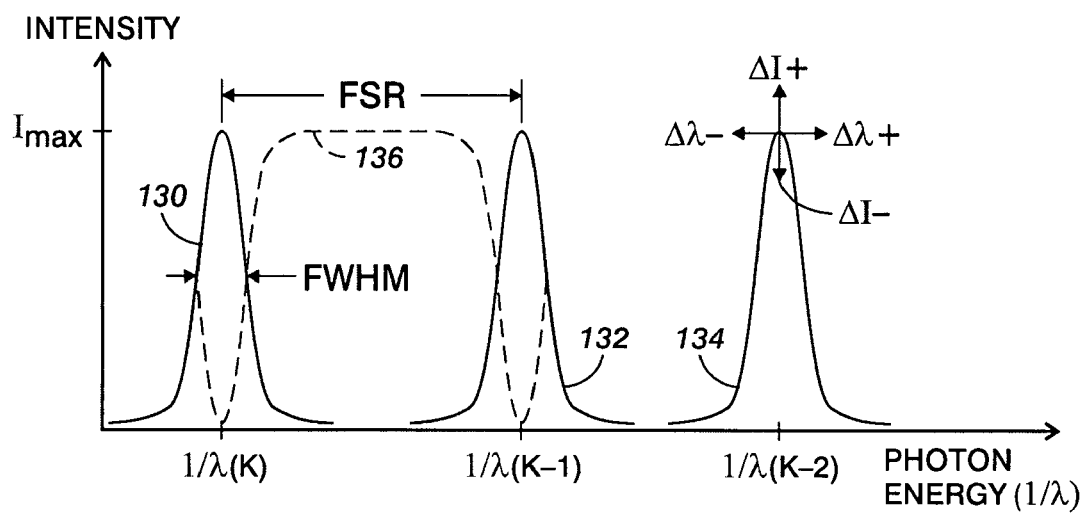
FIG. 3 is a graph showing intensity-energy curves for transmission and reflection from a cavity as in FIG. 2 when operated as a Fabry-Perot cavity, showing ways in which information can be included in transmission mode peaks.

FIG. 3 is an intensity-energy graph or "output spectrum" for optical cavity 100 when operated as a Fabry-Perot cavity such as an interferometer. Since photon energy is inversely proportional to wavelength, wavelength increases as one moves leftward along the horizontal axis, while the inverse of the wavelength ($1/\lambda$) increases as one moves rightward, as suggested by the labeling of points on the horizontal axis; it follows that energy and frequency would also increase to the right.

The graph in FIG. 3 includes a solid-line curve with peaks 130, 132, and 134, each of which is an "intensity-energy peak" or simply "intensity peak" that results from a respective transmission mode of cavity 100, illustratively the Kth, (K−1)th, and (K−2)th modes, and has an amplitude Imax, which could result from broadband illumination in the photon energy subranges of all the modes shown; such a curve is sometimes referred to herein as a "transmission spectrum". FIG. 3 also includes part of dashed-line curve 136 that is the complement of the transmission spectrum, i.e. the intensity-energy curve for light that is reflected rather than transmitted by optical cavity 100; such a curve is sometimes referred to herein as a "reflection spectrum" and its reflection modes are broad and separated by narrow valleys rather than being narrow peaks separated by broad valleys like the transmission modes. The term "output modes" is sometimes used herein as a generic term that encompasses transmission modes and reflection modes.

The maxima of intensity-energy peaks 130, 132, and 134 (and the complementary minima between reflection bands) are spaced apart as a function of photon energy (illustratively wavelength), and the difference between the central energy of adjacent transmission mode peaks is referred to as "free spectral range" or "FSR". FSR can be treated as the bandwidth over which adjacent intensity-energy peaks do not overlap, while the full width half maximum (FWHM) of the peaks can be treated as the minimum resolvable bandwidth. FSR, FWHM, and their ratio are all sometimes treated as figures of merit in designing a Fabry-Perot cavity.

The wavelength $\lambda$ of each intensity-energy peak can be obtained from $\lambda(k)=2nD/k$, where n is the refractive index of the cavity and k is a non-zero integer. Therefore, if refractive index of the cavity changes, $\lambda(k)$ also changes for a given value of k, so that if a peak's central energy changes, as indicated by $\Delta\lambda+$ and $\Delta\lambda-$ for peak 134, the change provides information about refractive index change. Similarly, the intensity of the peaks depends on absorption in the cavity, so that if the intensity of a peak departs from Imax, as indicated by $\Delta I+$ and $\Delta I-$ for peak 134, the change provides information about absorption change.

Figure 4:
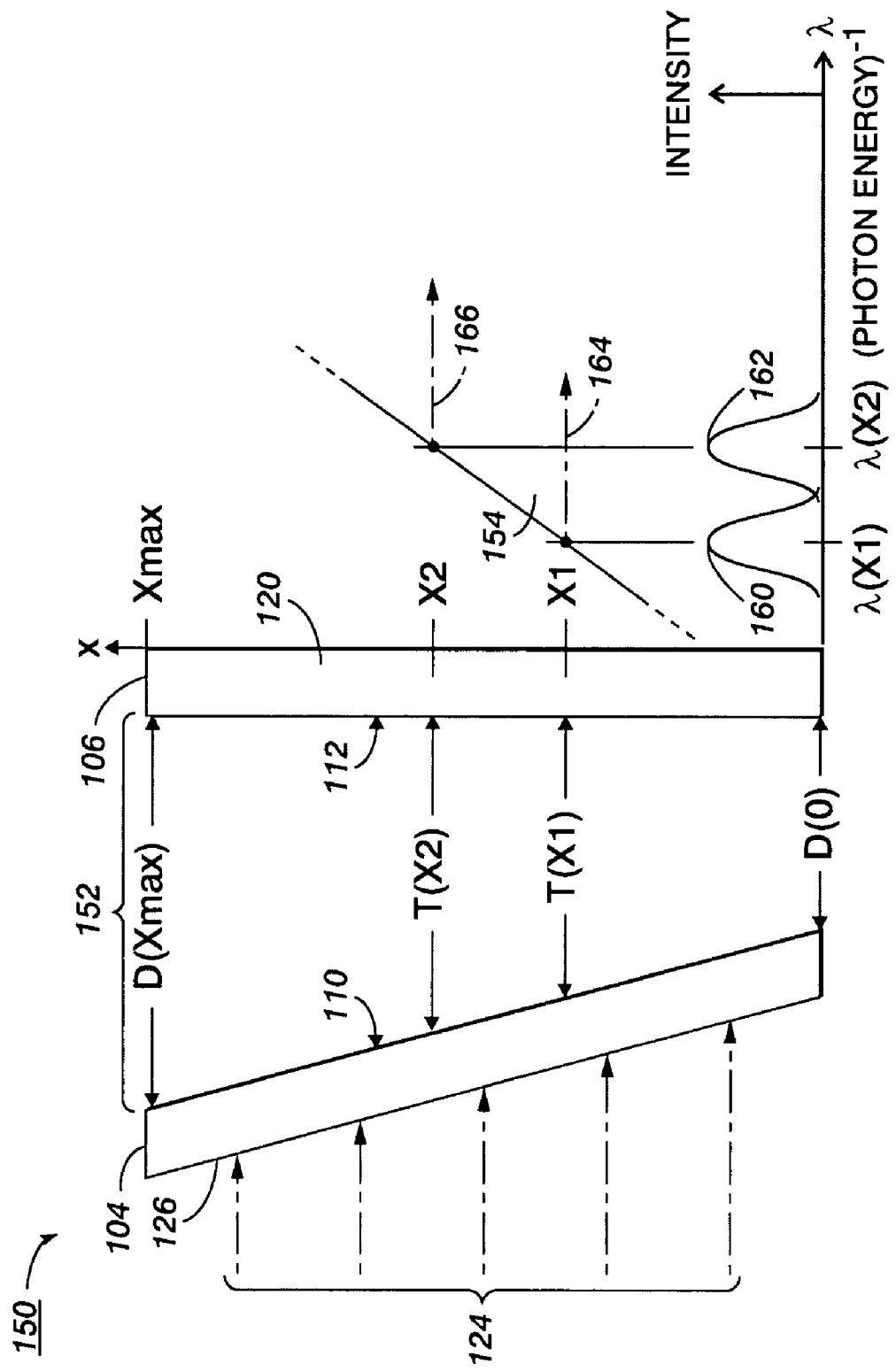
FIG. 4 is a schematic side view of a graded optical cavity that is an example of an inhomogeneous optical cavity that could be used in the system of FIG. 1.

FIG. 4 illustrates graded optical cavity 150, an example of an "inhomogeneous optical cavity", meaning a cavity that does not meet the above definition of a homogeneous optical cavity. Because of the similarities between cavities 150 and 100, parts and components of cavity 150 that are substantially the same as those in FIG. 2 are labeled with the same reference numbers. In cavity 150, however, region 152 is not homogeneous, but rather has "laterally varying optical distance" between reflective surfaces, meaning that the optical distance varies in one or more lateral directions; in the illustrated example, the optical distance illustratively increases linearly from D(0) at one end of cavity 150 (x=0) to D(Xmax) at the opposite end (x=Xmax), but optical distance between reflective surfaces in an inhomogeneous optical cavity could vary laterally in any appropriate way, and need not vary monotonically, linearly, or with any other type of uniformity.

Because of its linearly varying optical distance or thickness, cavity 150 can operate as a linearly variable optical filter or linear variable filter (LVF), a type of transmissive cavity. This capability is illustrated by the function T(x), a "laterally varying energy output function", meaning that photon energies of output light depend on lateral position; in this case, the function relates output photon energy (in response to input light represented by illumination arrows 124) to lateral position on exit surface 120. For an LVF, the simple relationship $\lambda(x)=T(x)=d'x+\lambda(0)$ can hold, where d' is a constant that depends on gradient of optical thickness and can be graphically represented by the constant slope $(\lambda(X2)-\lambda(X1))/(X2-X1))$ of position-wavelength graph 154 at right in FIG. 4.

In general, the characteristics of output light at each position on surface 120 can be a function of parameters other than optical thickness, including, for example, photon energy and incident direction of input light 124 received at counterpart positions on surface 126. In particular, the output light may depend on whether the input light is narrow band, broad band, or multi-modal, as can result from a set of transmission or reflection modes. Narrow band or multi-modal illumination of an LVF, for example, can produce one or several output light spots, respectively.

The graphs at right in FIG. 4 also illustrate intensity-energy peaks 160 and 162 that would result if cavity 150 were illuminated by narrow band input light with central energy of λ(X1) and λ(X2), respectively, and, in response, operated as an LVF as described above. At position X1, for example, T(X1) results in transmission of output light represented by arrow 164, within a photon energy subrange characterized by central energy λ(X1); at position X2, T(X2) results in transmission of output light represented by arrow 166, within a photon energy subrange characterized by central energy λ(X2); for the illustrated laterally varying energy output function, if X1≠X2 and the difference between X2 and X1 is sufficient, then T(X1)≠T(X2), and λ(X1)≠λ(X2). On the other hand, for relatively small regions of output surface 120, cavity 150 might in some cases operate locally as a homogeneous cavity with transmission modes as illustrated in FIG. 3. It follows that parameters applicable to transmission modes are sometimes also useful for intensity-energy peaks from inhomogeneous cavities; in particular, information about changes in refractive index and absorption can sometimes be provided through changes in intensity-energy peaks in ways shown in FIG. 3. Often, however, output light from an inhomogeneous cavity is more easily represented with an intensity-position graph, an example of which is described below.

Various techniques can be used to operate optical cavities to produce "laterally varying photon energy distributions" or simply "laterally varying energy distributions", meaning distributions in which photon energy of light varies as a function of lateral position. Such distributions can be produced, for example, with inhomogeneous optical cavities having laterally varying optical thicknesses and, even with homogeneous optical cavities, with angled illumination from a point light source rather than perpendicular illumination; several possible techniques are described in co-pending U.S. patent application Ser. No. 11/316,438, entitled "Photosensing Throughout Energy Range and in Subranges" and incorporated herein by reference in its entirety.

More generally, an inhomogeneous optical cavity can have any appropriate laterally varying energy output function, including functions that are nonlinear or nonuniform in other ways. Some of the below-described implementations, for example, involve functions that are affected by presence of an analyte in an optical cavity. As with homogeneous cavities, an inhomogeneous cavity's light-transmissive region can be completely between and partially bounded by light-reflective components as in FIG. 4, but partially and completely bounded light-transmissive regions with various other shapes and arrangements are possible.

Figure 5:
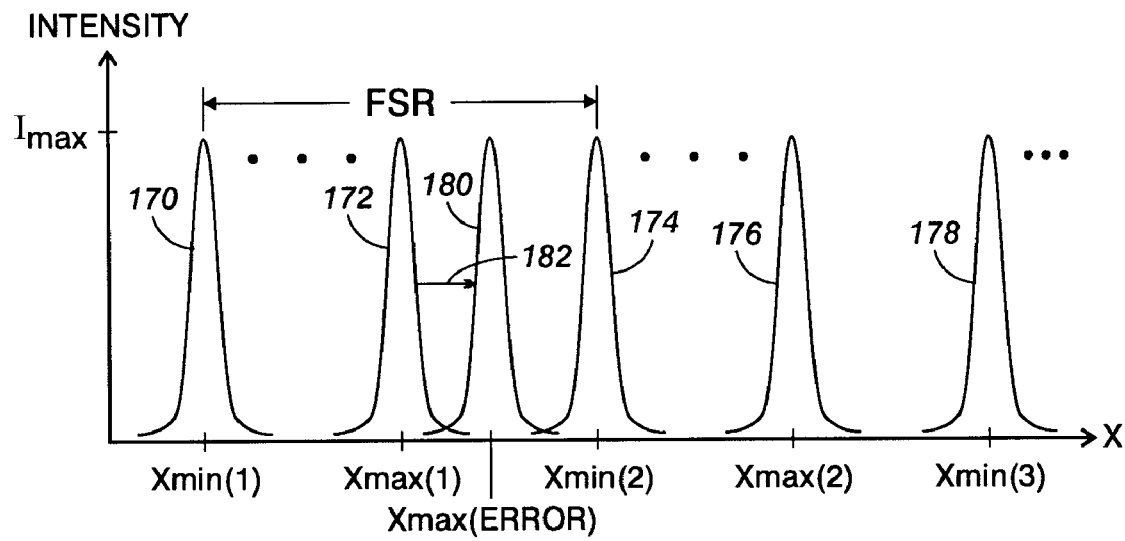
FIG. 5 is a graph showing an intensity-position function of a cavity as in FIG. 4, showing both spectral and harmonic relationships between peaks.

FIG. 5 is an intensity-position graph for optical cavity 150 when operated as a Fabry-Perot cavity such as an interferometer. FIG. 5 is similar to FIG. 3, and the peaks illustratively have maximum amplitude Imax as in FIG. 3 and their central energies and amplitudes (and FWHMs) could be affected as shown for peak 134 in FIG. 3, and their contrasts could also be affected; but the x-axis in FIG. 5 represents position in the x-direction in FIG. 4 rather than photon energy.

In the example shown in FIG. 5, cavity 150 is illuminated at P (P≧2) photon energies ranging from λmin to λmax, resulting in a series of output modes (illustratively transmission modes) for each photon energy λ(p) of illumination at those positions on the x-axis where the condition λ(p)=2n*D(x)/k is satisfied for integer values of k. The first transmission mode shown for λmin is peak 170 at x=Xmin(1) and for λmax is peak 172 at x=Xmax(1). The second transmission mode shown for λmin is peak 174 at x=Xmin(2) and for λmax is peak 176 at x=Xmax(2). The third transmission mode shown for λmin is peak 178 at x=Xmin(3), and so forth.

In the example of FIG. 5, transmission modes are sufficiently separated along the x-axis to prevent interference between adjacent transmission modes. As can be seen, Xmin(2) is sufficiently greater than Xmax(1) that peaks 172 and 174 do not interfere, and Xmin(3) is similarly sufficiently greater than Xmax(2) that peaks 176 and 178 do not interfere. If instead the first transmission mode of λmax were peak 180 due to an increase from Xmax(1) to Xmax(error), as indicated by arrow 182, interference between peaks 180 and 174 would begin to occur; as the first transmission mode of λmax increased further, loss of information would occur due to ambiguity between peak 180 and peak 174. Problems of this type can be avoided by coordination of photon energy range with cavity parameters; for example, cavity thickness D can be sufficiently small that only one output mode occurs over the range from λmin to λmax. The free spatial range (FSR) between the modes in a particular wavelength range can also be increased by reducing the tilt of the inhomogeneous (graded) cavity.

Figure 6:
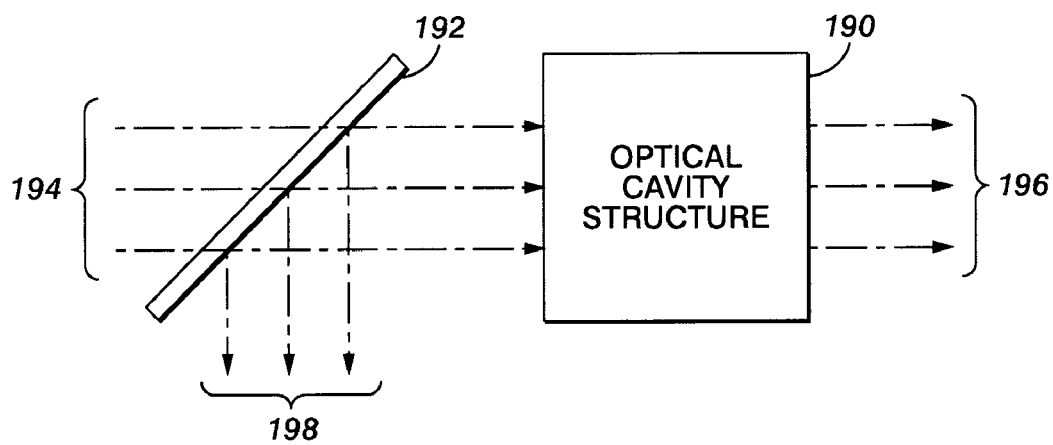
FIG. 6 is a schematic diagram of a setup in which an optical cavity as in FIG. 2 or 4 could operate to provide output light with reflection modes.

FIG. 6 shows a setup in which optical cavity structure 190 receives input light represented by arrows 192 through beam splitter 194. Optical cavity structure 190 can include a transmissive cavity implemented as in any of the ways described in relation to FIGS. 2-5 or in any other suitable way. In response to the input light, the cavity provides a transmitted portion of output light represented by arrows 196 and a reflected portion of output light represented by arrows 198. The use of beam splitter 194 is merely illustrative of ways in which input light and reflected light could be separated; for example, input light could be incident upon an entry surface at a sufficiently large angle from the normal that reflected light is separated from input light, though the non-perpendicular angle of incidence reduces performance of the optical cavity.

As suggested above in relation to FIG. 3, refractive index changes in the optical cavity will cause the same shift in both transmitted and reflected modes, while absorption in the optical cavity will similarly cause decreased amplitude and contrast and increased FWHM in both portions, with the effect of absorption typically varying as a function of photon energy; a curve showing absorption as a function of photon energy is sometimes referred to herein as an "absorption spectrum".

Figure 7:
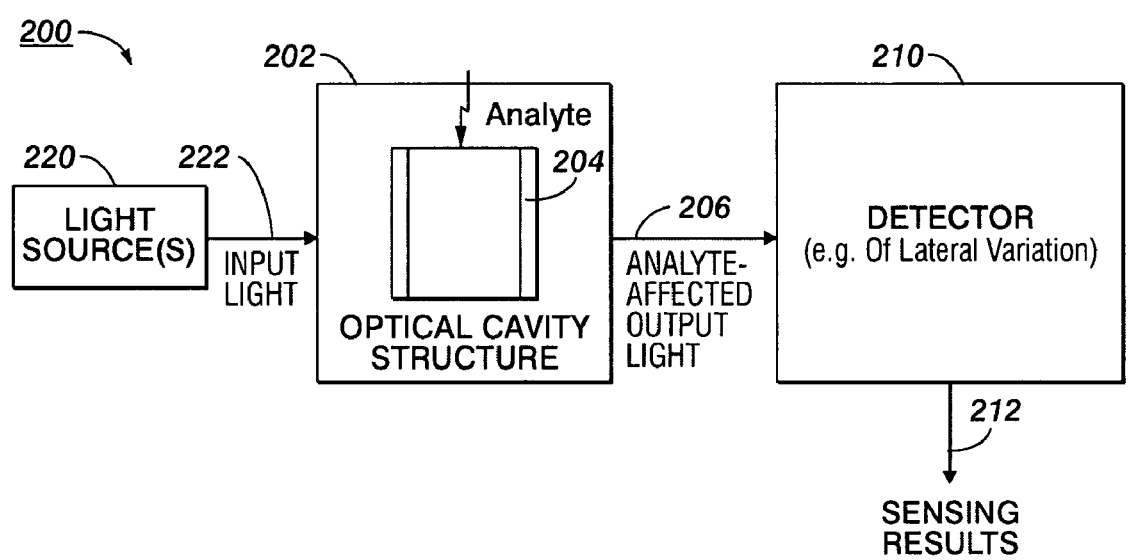
FIG. 7 is a schematic diagram of an implementation of the system of FIG. 1.

FIG. 7 shows system 200, an exemplary implementation of system 100 in FIG. 1. System 200 includes optical cavity structure 202, a structure that can include one or more optical cavities with features described above. In system 200, at least one of the optical cavities in structure 202, represented schematically by cavity 204, can contain an analyte, illustratively being provided to cavity 204. The presence of analyte in cavity 204 affects the output light provided by structure 202, and the analyte-affected output light, represented by arrow 206, can then be photosensed within detector 210. For example, detector 210 may include a photosensing component with one or more photosensitive surfaces at which lateral variation of light is detected, such as after the light passes through an LVF. The sensing results from detector 210 can be provided to other components within system 200 or to external components, as represented by arrow 212.

Detector 210 could be implemented in many different ways, such as with a photosensing IC, as described in co-pending U.S. patent application Ser. No. 11/702,250, entitled "Photosensing Optical Cavity Output Light" and incorporated by reference herein in its entirety. The implementation in FIG. 7 might, however, alternatively be implemented with photosensing components that do not include photosensing ICs, such as with one or more discrete photodiodes.

Although cavity 204 can be any suitable type of homogeneous or inhomogeneous optical cavity, including an emitting cavity or a transmissive cavity, FIG. 7 illustratively shows one or more light sources 220 that can be included within system 200 to illuminate one or more optical cavities. As represented by arrow 222, structure 202 receives input light from light sources 220. If optical cavity 204 is illuminated as shown, the analyte-affected output light represented by arrow 206 could include one or both of transmitted and reflected light.

Figure 8:
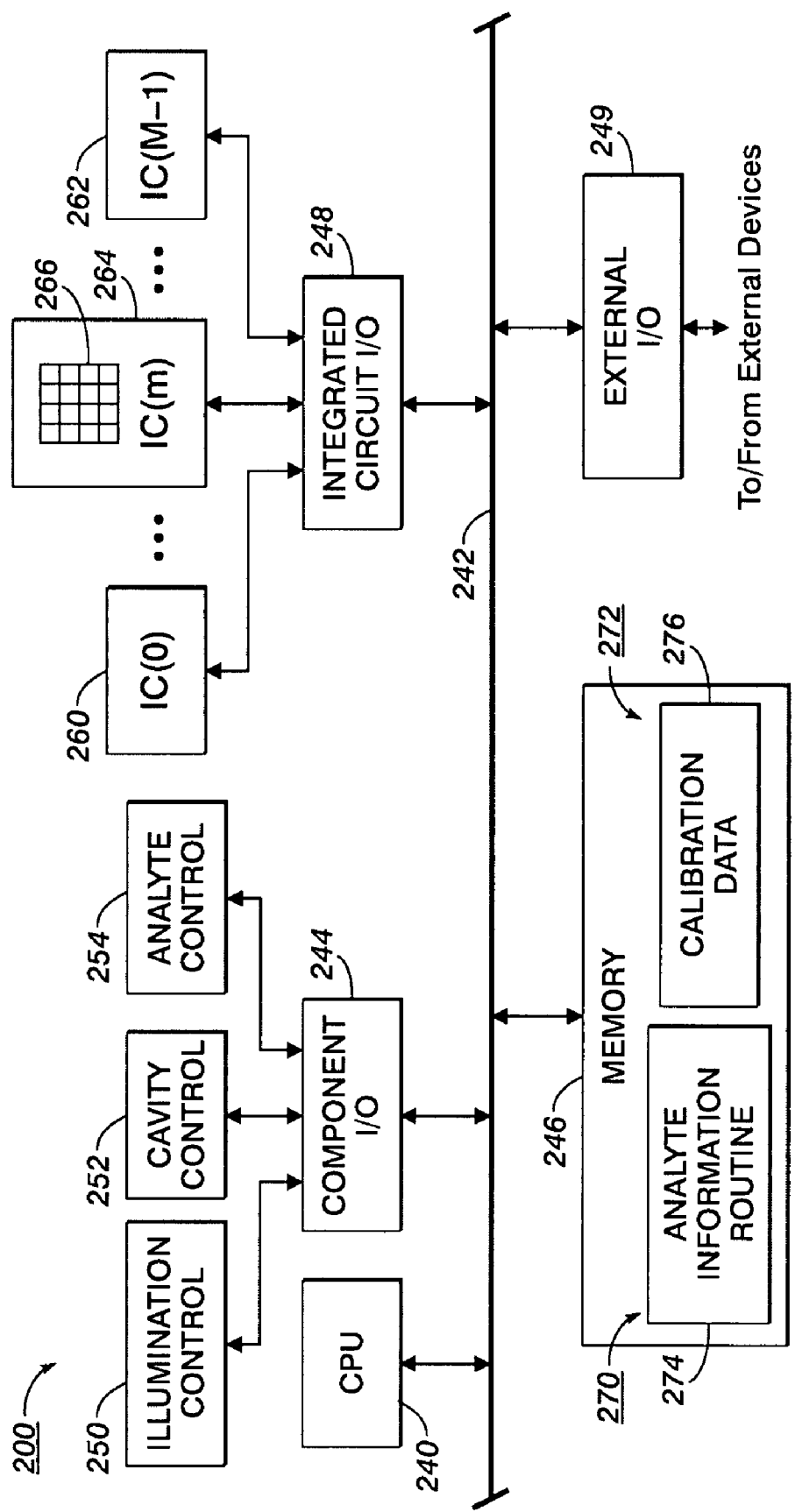
FIG. 8 is a schematic circuit diagram of a system implemented as in FIG. 7.

FIG. 8 illustrates electrical components that can be used in implementing system 200 as in FIG. 7. System 200 illustratively includes central processing unit (CPU) 240 connected to various components through bus 242, but a wide variety of other architectures could be employed, including any appropriate combination of hardware and software, as well as specialized hardware components such as application specific integrated circuits (ASICs) for one or more of the illustrated components or in place of a software component executed by CPU 240.

System 200 also includes component input/output (I/O) component 244, memory 246, integrated circuit input/output (IC I/O) 248, and external I/O 249, all connected to bus 242. System 200 can include various other components (not shown) connected to bus 242. In addition to connections through external I/O 249 by which signals can be provided to and received from external devices, bus 242 can also be connected directly to components outside of system 200.

Component I/O 244 permits CPU 240 to communicate with certain components of system 200, illustratively including illumination control 250, cavity control 252, and analyte control 254. For interactive applications, component I/O 244 could also be connected to a suitable user interface, such as a monitor and keyboard (not shown). In the exemplary implementation in FIG. 7, illumination control 250 can include light sources 220 (FIG. 7) and circuitry for controlling them; cavity control 252 can include electrodes or other components that can be operated to control cavity 204 and other cavities and can also include circuitry connected to those components; and analyte control 254 can similarly include fluidic devices or other components that can operate to transfer analyte into, through, or out of cavity 204 or other cavities or to produce relative movement between analyte and an array or a cavity, and can also include circuitry connected to those devices and components.

In the illustrated implementation of system 200, IC I/O 248 is a similar I/O component that permits CPU 240 to communicate with one or more ICs, such as in detector 210 in FIG. 5. M ICs are illustrated by a series from IC(0) 260 to IC(M−1) 262, including IC(m) 264 with a photosensor array 266.

Memory 246 illustratively includes program memory 270 and data memory 272, although instructions for execution by CPU 240 and data access during execution of instructions could be provided in any suitable way, including through external devices or components. The routines stored in program memory 270 illustratively include analyte information routine 274. In addition, program memory 270 could store various additional routines and also subroutines (not shown) that CPU 240 could call in executing routine 274. Similarly, the data in data memory 272 illustratively include calibration data 276, but could include various additional items of data and data structures accessed by CPU 240.

In executing routine 274, CPU 240 can provide signals to cavity control 252 and to analyte control 254 so that an analyte is present in cavity 204, for example, with the analyte having optical characteristics that affect output light from cavity 204. CPU 240 can also provide signals to illumination control 250 so that cavity 204 is appropriately illuminated to provide analyte-affected output light. CPU 240 can also provide signals to each of ICs 260 through 262 to obtain sensing results that include information about the analyte in cavity 204. In an implementation with a position-sensitive detector (PSD), CPU 240 could instead provide whatever signals are necessary to obtain photosensed quantities from the PSD; for example, CPU 240 could control circuitry to connect output currents from the PSD to a differential amplifier.

Figure 9:
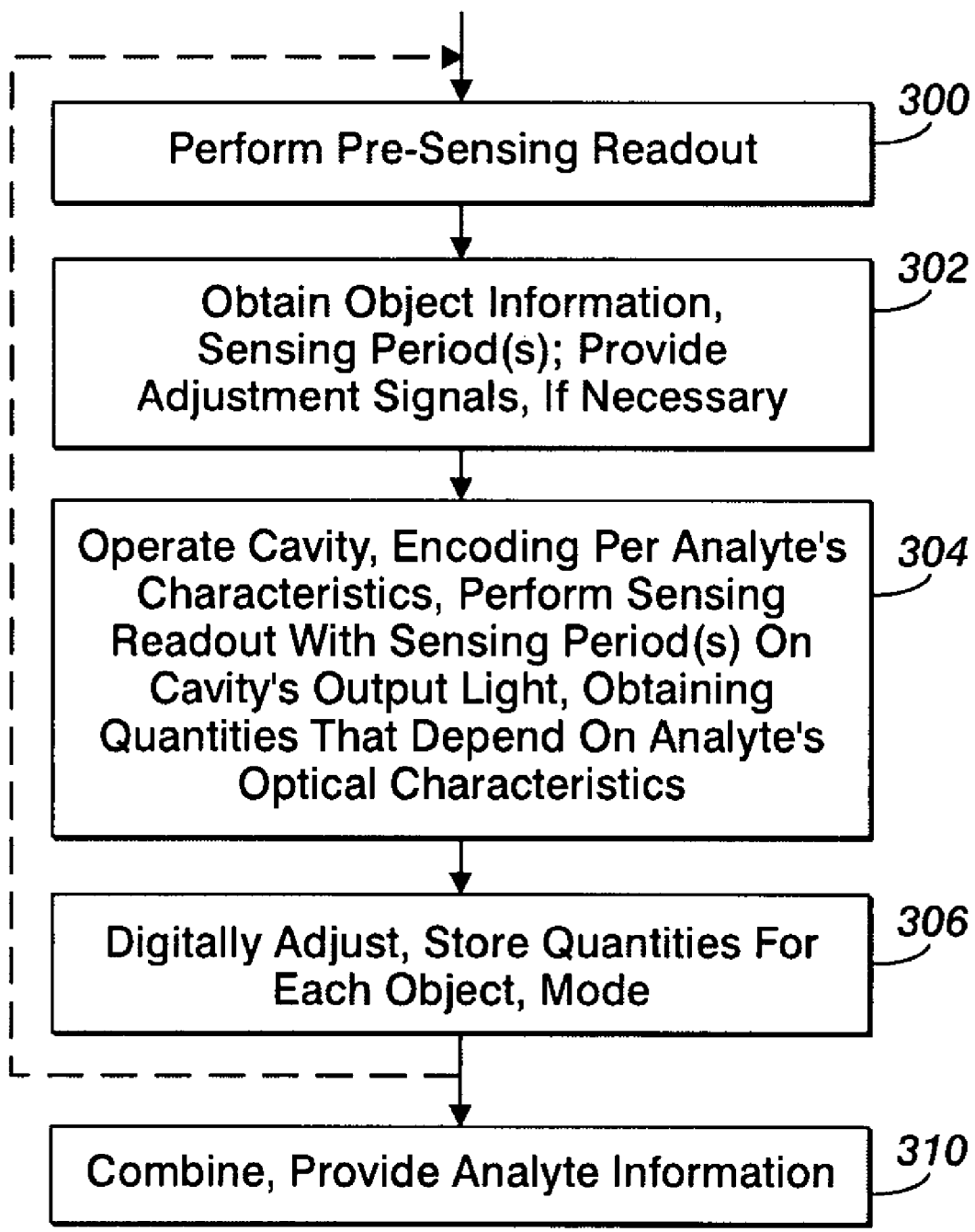
FIG. 9 is a flow diagram showing operations of the analyte information routine in FIG. 8.

FIG. 9 illustrates one example of how analyte information routine 274 could be implemented in a system like system 200 in FIGS. 7 and 8. The routine in FIG. 9 could be implemented for single objects moving along paths through cavities past arrays; for spaced multiple objects moving along paths through cavities past arrays; or for continuous streams of objects, such as small volumes of fluid, moving along paths through cavities past arrays, in each case subject to appropriate constraints and with the cavities providing output energy distributions that include information about analytes in objects, such as laterally varying energy distributions if an inhomogeneous cavity.

Examples of objects that could occur in implementations as described herein include droplets, bubbles, small volumes of fluid, single molecules, agglomerated molecules, molecule clusters, biological cells, viruses, bacteria, proteins, DNA, microparticles, nanoparticles, and emulsions. A droplet or small volume of fluid may, for example, include atoms, molecules or other particles that affect refractive index, absorption, or other optical characteristics. An object "travels" or is caused "to travel" if the object moves through a succession of positions. For example, the object could be conveyed in a fluid, such as a liquid, gas, or aerosol, in which case the object may be referred to as being "carried by the fluid."

The term "path" is used herein to refer to a substantially continuous series of positions through which an object may travel. A path is "through a cavity" if an object following the path passes through part of the cavity. A photosensing component, such as an array or PSD, is "positioned along" or "along" a path through a cavity if the component is positioned near the cavity in such a way that, when an object following the path affects output light from the cavity, the photosensing component can obtain sensing results that include information about how the object is affecting the output light; it is not necessary, however, that the photosensing component be immediately against or adjacent to an external surface of the cavity that includes the path—there could, for example, be another optical cavity or other optical component between them, such as an LVF. An object following a path in a case where an array is along the path in any of these ways can be said to move "past the array".

The routine in FIG. 9 follows a general strategy of performing a series of readout operations, after which information is combined and provided. It would also be possible to provide the information from each readout operation immediately or to provide information both immediately after each readout operation and also after a series of readout operations.

When CPU 240 executes the operation in box 300, it performs a pre-sensing readout. The purpose is to obtain information necessary to later perform a sensing readout. The information could be obtained in the ways described in co-pending U.S. patent application Ser. No. 11/315,992, entitled "Sensing Photons from Objects in Channels" and incorporated herein by reference in its entirety.

Using the information from box 300, CPU 240 could obtain information about each object and determine an appropriate sensing period for each object, in the operation in box 302. For example, CPU 240 could perform calculations to determine whether one or more objects are present, the position of each object, and the speed of each object. Using this information and taking into account previously calculated sensing periods for the same objects, if any, CPU 240 can also determine an appropriate sensing period to be used during sensing readout; in general, the sensing period must provide an integration time shorter than the time necessary for an object to pass each cell in an array. Each object can therefore have a unique sensing period.

The operation in box 302 can also include providing any necessary signals through component I/O 244 to adjust movement of objects, such as by adjusting fluid speed; to adjust illumination or stimulation of the optical cavity; or to adjust characteristics of the optical cavity, such as by adjusting optical distances and/or tilt angles between light-reflective components. These signals could include any appropriate combination of signals to illumination control 250, cavity control 252, and analyte control 254. In particular, these signals could include providing tuning signals to a tuning structure to move light-reflective components relative to each other, as described above in relation to FIG. 1. Tuning signals could be provided to move light-reflective components to a distance from each other at which the optical cavity provides light with desired wavelengths or with desired transmission or reflection modes. Tuning signals could also be provided to tilt or otherwise modify orientation or, more generally, relative positions of light-reflective components to obtain a desired energy output function for an inhomogeneous optical cavity, as described in greater detail in co-pending U.S. patent application Ser. No. 11/702,320, entitled "Tuning Optical Cavities" and incorporated herein by reference in its entirety.

If the tuning structure includes electrodes as described below, the operation in box 302 can also include providing and monitoring signals to measure capacitance between electrodes, which provides information about distance between the electrodes. For example, CPU 240 could compare the measured capacitance with a fixed set point.

CPU 240 can then cause operation of the cavity in a way that encodes information about the analyte's optical characteristics and can also perform sensing readout on a cavity's output light, in box 304. This operation includes providing any further signals through component I/O 244 so that the cavity provides analyte-encoded output light and also providing signals through IC I/O 248 so that photons are photosensed cumulatively during the sensing period obtained in box 302. This operation can also include providing signals through component I/O 244 to encode particular kinds of information about analyte optical characteristics, such as to directly encode absorption spectrum derivative or refractive index dispersion derivative by continuously modulating cavity thickness during measurement or to encode values at a series of sampling points by gradually scanning the cavity across a range of wavelengths at discrete intervals or in small increments that approximate a continuous scan, as could be useful in obtaining a spectrum. Furthermore, cavity thickness and/or tilt could be modulated periodically to obtain lock-in with a readout signal having the same modulation frequency, to improve signal-to-noise ratio and increase sensitivity, as described below.

If the tuning structure includes electrodes as described below, the operation in box 304 can also include providing and monitoring signals to measure capacitance between electrodes, which provides information about distance between the electrodes. For example, CPU 240 could compare the measured capacitance with a fixed set point, or could monitor periodic or other variations in capacitance to optimize measurements.

During this operation, CPU 240 may also provide signals to peripheral circuitry on an IC so that analog quantities photosensed by cells are adjusted based on reference values. After adjustment, if any, analog quantities can be converted to digital signals for readout. The operation in box 304 can be implemented in whatever manner is appropriate for a given photosensing IC, whether a CCD or CMOS implementation, and regardless of whether readout is purely serial or is also parallel.

Since an analyte's optical characteristics can affect the output light provided from a mode of an optical cavity, such as in the ways described above in relation to FIGS. 1, 3, and 5, information about the optical characteristics is present in the cavity's output light, encoded in intensity functions of one or more modes and in a laterally varying energy distribution. Sensing results obtained in box 304 can therefore include part or all of the encoded information, in the form of photosensed quantities that depend on the analyte's optical characteristics. For example, the sensing results can include information about at least one of position, size, and intensity of a light spot and, accordingly, about the respective mode's intensity peak. If the output light from the cavity includes intensity peaks for two or more modes, their respective light spots can be tracked separately as described below.

The photosensed quantities read out in box 304 can also be digitally adjusted by CPU 240 before being stored for each object and mode, in box 306. The digital adjustment can include adjusting quantities photosensed by cells based on reference quantities or based on calibration data 276 (FIG. 8), and can also include any necessary adjustments due to differences in sensing periods or other factors; calibration-based techniques that can be used are described in co-pending U.S. patent application Ser. No. 11/633,302, entitled "Position-based Response to Light" and incorporated herein by reference in its entirety.

The digital adjustment in box 306 and the analog adjustment, if any, in box 304 can also employ reference cell-based adjustment techniques described in co-pending U.S. patent application Ser. No. 11/316,438, entitled "Photosensing Throughout Energy Range and in Subranges" and incorporated herein by reference in its entirety; such reference cell-based adjustment techniques may be especially useful for intensity referencing and in tracking an object's position. In particular, such adjustments can be used to overcome problems with inhomogeneous illumination, but such techniques may be difficult to implement successfully in system 200 because external inhomogeneities that affect output light, such as in illumination or in stable or time-varying absorption by particles between light sources 220 and optical cavity 204, are not readily distinguishable from absorption within cavity 204. In other words, adjustment based on reference cells may remove desired information about absorption changes inside cavity 204.

To avoid this and other such problems, the operation in box 306 or a subsequent operation can make an alternative data manipulation or adjustment to obtain "cavity-only absorption data", an expression that refers herein to values or other data in which information about absorption in cavity 204 is preserved while information is reduced about features exterior to cavity 204 such as inhomogeneities in illumination and external absorption, operating as described in co-pending U.S. patent application Ser. No. 11/702,249, entitled "Obtaining Information From Optical Cavity Output Light" and incorporated herein by reference in its entirety. As will be understood, the encoding of absorption information in the manner described allows removal of noise-like effects other than those from absorption coefficient inside cavity 204, influences such as external perturbations, disturbances, or inhomogeneities. As a result, measurements of absorption can have a higher signal to noise ratio. Also, information can be recovered from analyte-encoded output light that is selectively sensitive to absorption changes inside cavity 204.

Other adjustment techniques that can be used, such as in box 306, are described in co-pending U.S. patent application Ser. No. 11/702,329, entitled "Implanting Optical Cavity Structures" and in co-pending U.S. patent application Ser. No. 11/702,325, entitled "Containing Analyte In Optical Cavity Structures", both of which are incorporated herein by reference in their entireties.

Orientation of components can result in non-perpendicular incidence of input light on optical cavities, such as if an operation in one of boxes 302 and 304 changes the tilt of the entry surface at which a cavity receives incident light. Unless all output light is incident on one position of the detector component or the detector component has only a single large area as with some PSDs, adjustments can be made to correct for non-perpendicular incidence of input light: For example, if the light source component emits light from a point source at many different angles that are accordingly transmitted through the cavities at various angles, the detector component's photosensitive surface receives the output light at many different angles, but each cell of a photosensor array would receive only a very small angular distribution; therefore, if the angle could be known, as would be the case in a fixed geometry but may not be the case in FIG. 7, the angle-induced variation can be easily corrected.

The position and speed information about each object from box 302 can be used by the operation in box 306 to determine which photosensed quantities result from effects of each object. Similar techniques can be used to determine which photosensed quantities result from each mode's light spot when a cavity's output light includes two or more modes.

For homogeneous analyte in cavity 204 or for stationary or slow-moving objects in cavity 204, lock-in techniques could be applied to further improve signal to noise ratio, such as by modifying operations in boxes 302, 304, and 306 in FIG. 9. For example, illumination from light sources 220 can be modulated in order to modulate output light from cavity 204. Or, as described above, cavity thickness and/or tilt can be modulated, in effect modulating characteristics of the cavity. The applicable modulation frequencies would be constrained by the readout frequency achievable by detector 210; rapid readout may be available, for example, with photosensing components that provide differential signals in response to position changes on a photosensitive surface, some examples of which are described in greater detail in co-pending U.S. patent application Ser. No. 11/633,302, entitled "Position-based Response to Light" and incorporated herein by reference in its entirety—differential signal techniques may also have very high sensitivity as could be necessary to determine extremely small refractive index changes of analyte in a cavity. In implementations where it is not possible to directly record a correlation signal, another type of reference could be used, such as an empty channel in a fluidic structure, a channel with a reference medium, or an uncoated reference cell in a photosensing array with coated cells to sense photon energy subranges.

In performing the operations in boxes 304 and 306, CPU 240 can employ data structures (not shown) stored in memory 246. For example, one data structure can store each object's previously calculated position and speed, which can then be used in performing subsequent calculations to identify effects of the same object; similarly, each object's data structure can also include each light spot's identifying information and the object's effect on the identified light spot, which can similarly be used in subsequent calculations. Also, a readout data structure can be employed to hold all of the adjusted quantity information about each object.

The operation in box 306 can update the readout data structure each time it obtains additional information about the same object. In an implementation as in FIG. 8, the operations in boxes 300, 302, 304, and 306 can be performed separately for each of ICs 260 through 262. Further, as suggested by the dashed line from box 306 to box 300, the same operations can be performed repeatedly for each of the ICs. If each object can be correctly identified throughout its travel along a path through cavity 204, the readout data structure can be used to hold all of the information obtained from all ICs. Between consecutive executions of the operations in boxes 300, 302, 304, and 306, the effects of each object may move only a few cells along the path, and consecutive objects must be sufficiently separated to avoid confusion. For example, each object may be a few μm in diameter, each cell may have a length along the path of between 10 and 20 μm, and consecutive objects may be two or three cell lengths apart. For larger objects or for cells of different sizes, the spacing between consecutive objects can be adjusted appropriately.

Various modifications could be made in the implementation of FIG. 9. For example, rather than being spaced apart, objects could be closer together. Even if several objects are having overlapping effects on a light spot, it may be possible to perform computational algorithms to separate the effects of the objects. Similarly, if objects are very close to each other but positioned along different cells, an optical structure between the path of the objects and detector 210 could ensure that photons affected by different objects travel to different cells; in this way, a continuous stream of objects could be measured. Furthermore, techniques as described above could be applied to a continuous fluidic stream without distinguishable objects in it, in which case the analyte-affected output light from optical cavity 204 would be determined by optical characteristics of concentrations of molecules in each position in the stream rather than by optical characteristics of distinguishable objects. In effect, the stream would be divided into imaginary small volumes, each of which would be an object analyzed as described above, allowing for continuous monitoring of how the output light from the fluid changes with time, such as due to changing composition of the fluid.

As the operations in boxes 300, 302, 304, and 306 are repeated while an object travels along a path past detector 210, more and more information is obtained, especially where a cavity's output light has more than one light spot, with each light spot having a respective position on the array. When the object has passed the whole array, information about the analyte it contains can be recomposed from the stored fractions.

Upon completion of any suitable amount of information gathering in boxes 300, 302, 304, and 306, CPU 240 can perform the operation in box 310 to provide analyte information, such as in the form of data for another routine or as output through external I/O 249. As shown, this operation can include combining the sensed quantities for each object so that analyte information for the object can be provided, such as in the form of an absorption spectrum, a value for the analyte's refractive index, or some other data structure. Further description of information obtaining techniques is provided in co-pending U.S. patent application Ser. No. 11/702, 249, entitled "Obtaining Information From Optical Cavity Output Light" and incorporated herein by reference in its entirety.

Many possible uses exist for analyte information as obtained in box 310, and operations like those in FIG. 9 could be implemented with a wide variety of existing technologies;

analyte information could be used, for example, to distinguish objects, as described in detail in co-pending U.S. patent application Ser. No. 11/702,328, entitled "Distinguishing Objects" or to detect glucose in bodily fluids, such as with techniques described in co-pending U.S. patent application Ser. No. 11/702,329, entitled "Implanting Optical Cavity Structures", both of which are incorporated herein by reference in their entireties. Furthermore, it is foreseeable that further uses of analyte information and technologies for implementing such operations will be developed in the future. In general, analyte information from box 310 can be used in any way whatsoever, including not only existing techniques but also techniques developed hereafter. The operations illustrated in FIG. 9 do not require any specific technology, such as for data storing or processing operation, and are compatible with any such technology that exists now or may be hereafter developed.

Figure 10:
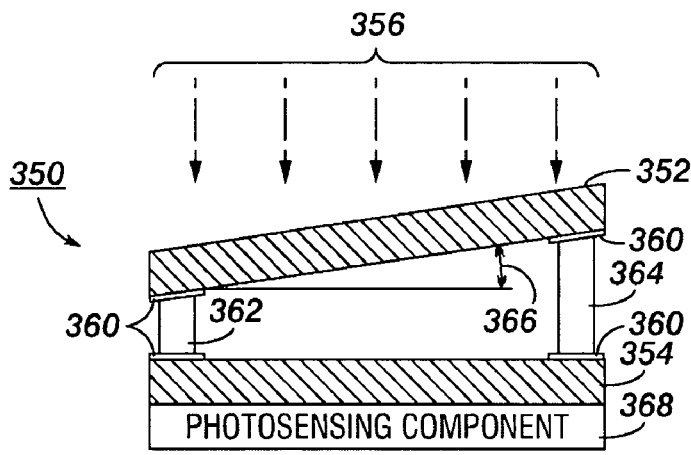
FIG. 10 is a schematic side view of a device with an optical cavity that can be tuned by modifying the length of elastomer spacers and could be used in a system as in FIGS. 7 and 8.

FIG. 10 shows device 350, which can also be used in a system as in FIGS. 7 and 8. Light-reflective components 352 and 354, together with the region between them, can operate as an inhomogeneous optical cavity as shown when illuminated by input light, represented by arrows 356, and could also operate as a homogeneous optical cavity, potentially even as a laser without an external light source if a suitable gain medium is positioned in the light-transmissive region between components 352 and 354 and if components 352 and 354 can be held sufficiently parallel.

Components 352 and 354 have electrodes 360 on their inward surfaces, facing each other and with deformable spacers 362 and 364 between them, electrodes 360 can, for example, be metal or other conductive material. As a result, signals can be provided to electrodes 360 to cause changes in distances between the inward, reflective surfaces of components 342 and 344, such as electrostatically, electromagnetically, or piezoelectrically, changing the shape of the region between them, as suggested by angle 366. For example, one or both of the electrodes 360 at the ends of each of spacers 362 and 364 can be independently addressable from those at the ends of the other spacers, so that each spacer can be independently deformed, such as to change angle 366 or change optical thickness of the cavity. In exemplary electrostatic implementations in which spacers 362 and 364 include dielectric elastomer material, voltage signals can cause attraction and repulsion between electrodes 360 and also electrostrictive forces in the elastomer, in turn causing deformation of spacers 362 and 364; in microelectromechanical systems (MEMS) switch implementations, however, one electrode in each pair is usually grounded while the other can be charged with either polarity to produce attraction (but not repulsion)—the resulting deformation brings the pair of electrodes toward each other, and when attraction ends they then move away from each other due to elasticity. In exemplary electromagnetic implementations in which spacers 362 and 364 include nonmagnetic elastomer material, each of electrodes 360 includes an embedded or otherwise attached electromagnet (not shown) oriented and electrically connected so that electrical signals through electrodes 360 can produce attraction and repulsion between electromagnets, similarly causing compression or expansion of spacers 362 and 364. In exemplary piezoelectric implementations in which spacers 362 and 364 include piezoelectric material, spacers 362 and 364 contract or expand in response to electrical signals received through electrodes 360. In addition to these examples, deformable components with various other materials could be implemented.

An independent voltage signal could be applied to each electrode to cause a desired deformation, with the specific signal depending both on the deformation and also on the manner in which deformation is produced; alternatively, one or more larger electrodes could be at one side of the cavity, and independent voltage signals could be applied to smaller electrodes on the other side, to different parts of each larger electrode, or in a delay-line technique that would propagate across each larger electrode. Calibration as described below could be performed to determine the specific voltage required across a given electrode pair to produce a specific distance between the electrodes, and the results could be included in calibration data 274 (FIG. 8). Since the distance between electrodes corresponds closely with cavity thickness and since cavity thickness determines the range of transmitted wavelengths, calibration can be based on transmitted wavelengths rather than actual measurements of cavity thickness. In addition to transmitted wavelength, tuning can also control other optical characteristics of the optical cavity, including FSR, LVF gradient, and so forth.

In one experimental implementation, a layer of polydimethylsiloxane (PDMS) elastomer (which can be spin-coated up to 100 µm, a process that can also control surface roughness and flatness of metal mirror layers) was subjected to a voltage between highly reflective metal electrodes on its opposite sides, simulating an implementation with a single uniform spacer rather than separate spacers as in FIG. 10; a single spacer could be used because PDMS is transparent in the visible and infrared ranges, similarly to glass, so that it can be the light-transmissive region of an optical cavity. PDMS elastomer is incompressible with a modulus of elasticity approximately 0.5 MPa, but voltage across a PDMS layer causes electrostriction in the elastomer. In a 5 µm thick layer, 220V caused a thickness deformation of 200 nm, corresponding to a 4% change in cavity thickness and therefore approximately 4% shift of the Modes of a Fabry-Perot interferometer or etalon, e.g. from 686 nm to 713 nm.

The above experimental implementation demonstrates that widely tunable cavities can be fabricated with elastomer spacers between light-reflective components. Furthermore, with different dimensions, both in thickness and lateral extent, and with different elastomer material, even larger relative deformations should be achievable. Because the voltage needed to induce a given deformation depends on various factors including spacer thickness between electrodes, electrode quality, and the elastomer material used, it should be possible to reduce the required voltage significantly through optimization.

With independently addressable electrodes, device 350 can be tuned in a wide variety of ways: Tilt angle 366 can be increased to allow additional Fabry-Perot modes in an LVF; tilt angle 366 can be reduced to narrow the transmission range of an LVF, up to the limit in which it operates as a homogeneous cavity; tilt angle 366 can similarly be adjusted to accommodate a specific narrow band light source; thickness can be adjusted uniformly to shift the cavity's range; and so forth.

The distances between electrodes in each pair, indicative both of cavity thickness and of the angle of tilt, can be very precisely measured and controlled, such as by capacitive measurement, allowing adjustment of device 350 for a particular application and also allowing use of lock-in techniques. For this purpose, too, it is useful that the electrodes at the ends of each spacer are independently addressable. It would also be possible to have additional electrodes dedicated to obtaining capacitance measurements to measure distances between electrodes.

At positions where photon energy of input light is the same as a transmission mode of device 350, light is transmitted to photosensing component 368, which obtains sensing results. If analyte is present in the region between structures 352 and 354, optical cavity operation can provide analyte-affected output light, implementing features described above in relation to FIG. 1.

In the implementation illustrated in FIG. 10, light-reflective component 354 is shown directly on photosensing component 368, suggesting that component 354 could be fabricated directly on top of a photosensitive in a photosensing IC such as a photosensing array or a PSD, which could produce a very compact detector. In general, however, component 354 could be fabricated on a substrate, such as a glass slide, and one or more optical components could also be positioned between the substrate and photosensing component 368, to produce a desired light distribution on one or more photosensitive surfaces in photosensing component 368, as described in more detail for optical cavities that contain fluid analytes such as liquid, gas, or aerosol in co-pending U.S. patent application Ser. No. 11/702,325, entitled "Containing Analyte In Optical Cavity Structures" and incorporated herein by reference in its entirety.

Figure 11:
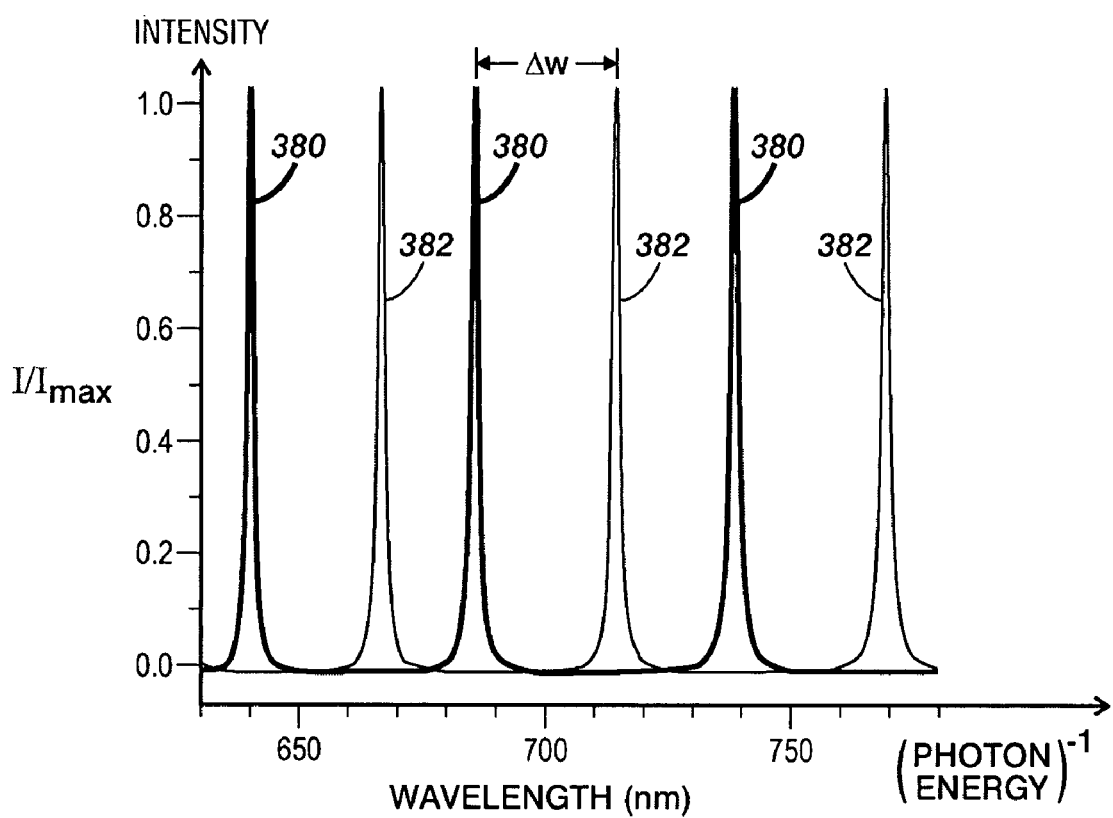
FIG. 11 is a graph showing two transmission spectra that could be provided by tuning an optical cavity as in FIG. 10.

FIG. 11 illustrates an example of how device 350 can be adjusted to obtain two different transmission spectra. The intensity-energy graph in FIG. 11 includes two curves: The curve that includes peaks 380 results from a spacing of 4.8 microns between structures 352 and 354, while the curve that includes peaks 382 results from a spacing of 5 microns. Mirror reflectivity of 95% was used. The resulting wavelength shift of approximately 30 nm corresponds to a relative change of the cavity thickness, which is similar to the 4% shift obtained experimentally, as described above. Although these curves indicate operation of device 350 as a homogeneous optical cavity, similar results would occur if it were operated as an inhomogeneous cavity as illustrated in FIG. 10, though an intensity-position graph would be more appropriate in that case. In either case, the output light could include information about optical characteristics of analyte in the region between structures 352 and 354, encoded as described above in relation to FIGS. 3 and 5.

The techniques in FIGS. 10 and 11 can be extended to obtain derivatives, either directly by recording mode intensity while continuously changing cavity thickness or indirectly by calculating slope between measurements of absorption or other optical characteristics at pairs of incrementally different photon energies obtained by tuning a homogeneous optical cavity that contains analyte. Similarly, cavity shape can be adjusted by such techniques to improve sensitivity; for example, sensitivity can be further increased if cavity thickness is periodically modulated with a small amplitude, also referred to as "wobbling", during continuous change of cavity thickness.

A device as in FIG. 10 can also be used for other purposes, such as to produce an optical cavity or transmission structure with desired characteristics. For example, a homogeneous or inhomogeneous optical cavity with desired optical thickness could be produced; similarly, a transmission structure that is an LVF with a desired gradient could be produced.

Tunable cavities that can contain analyte could be implemented in many ways besides the way illustrated in relation to FIGS. 10 and 11.

Figure 12:
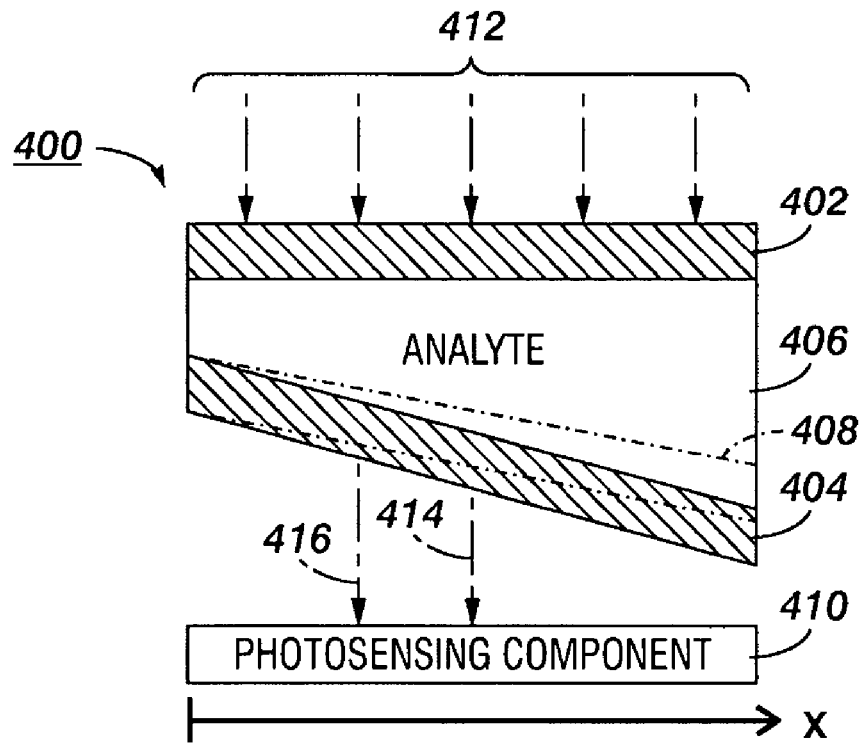
FIG. 12 is a schematic side view of a graded optical cavity that can contain analyte and could be used in a system as in FIGS. 7 and 8.

FIG. 12 shows device 400, which can also be used in a system as in FIGS. 7 and 8. Light-reflective components 402 and 404 provide reflection surfaces on either side of region 406, which can be filled with analyte as shown. By operating deformable components as described above in relation to FIGS. 1 and 10, light-reflective components 402 and 404 can be moved relative to each other, such as to change their relative orientations or "tilt angle", as suggested by dashed outline 408, illustrating a different position of component 404 relative to component 402. As described above, the distance between components 402 and 404 could similarly be changed.

FIG. 12 also shows photosensing component 410, which could be implemented as part of device 400 with or without one or more optical components between light-reflective component 404 and photosensing component 410, such as in the way illustrated in FIG. 10 or in the ways described in greater detail in co-pending U.S. patent application Ser. No. 11/702,325, entitled "Containing Analyte In Optical Cavity Structures" and incorporated herein by reference in its entirety. Alternatively, photosensing component 410 could be part of a separate device, such as in some of the techniques described in co-pending U.S. patent application Ser. No. 11/702,329, entitled "Implanting Optical Cavity Structures" and incorporated herein by reference in its entirety.

When device 400 receives input light, represented by arrows 412, through component 402, optical cavity operation can occur, resulting in transmission of analyte-affected output light to photosensing component 410; if appropriate, an LVF or other optical components could be positioned between light-reflective component 404 and photosensing component 410, such as for the reasons described in co-pending U.S. patent application Ser. No. 11/702,250, entitled "Photosensing Optical Cavity Output Light" and incorporated by reference herein in its entirety. The index of refraction of analyte in region 406 and the relative positioning of components 402 and 404 determine positions of light transmission, and illumination can be provided so that only one wavelength is transmitted but at varying output light positions, two of which are represented by arrows 414 and 416: Arrow 414 could, for example, represent output light provided when components 402 and 404 are in the position illustrated by component 404, while arrow 416 could represent output light provided when in the position illustrated by dashed outline 408.

Figure 13:
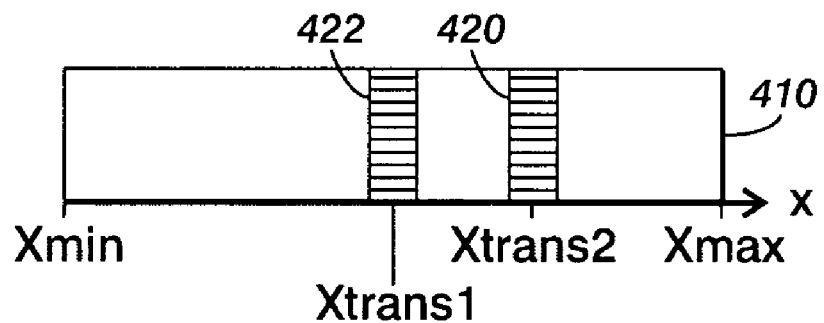
FIG. 13 is a schematic top view of a photosensing component as in FIG. 12.

FIG. 13 shows a similar example of the pattern of light on the upper surface of photosensing component 410 if the optical cavity were illuminated in only one narrow wavelength band. As shown, light spot 420 on photosensing component 410 indicates that the incident narrow band light is transmitted at a certain position Xtrans1. If the shape of the optical cavity changed due to movement of light-reflecting component 404, such as to the position of outline 408, the location of the transmitted light spot 420 would move, either toward Xmin, as shown by light spot 422 at Xtrans2, or toward Xmax. If analyte absorption changes, causing a change in intensity, contrast, and FWHM of output light's intensity function, the size and intensity of light spot 420 would change rather than its position.

Tunable optical cavities that contain analyte can be implemented in many ways in addition to the way illustrated in FIGS. 12 and 13. In many applications, an optical cavity structure as in FIG. 7 could be implemented to include one or more inhomogeneous optical cavities that contain analyte as in FIGS. 12-13. Furthermore, the optical cavity in device 400 could instead be a homogeneous optical cavity that contains analyte and that is operated to provide a laterally varying output energy distribution, by providing a range of angles at which input light is incident, as described in co-pending U.S. patent application Ser. No. 11/316,438, entitled "Photosensing Throughout Energy Range and in Subranges" and incorporated herein by reference in its entirety.

FIG. 14 illustrates exemplary operations in producing a device like devices 350 (FIG. 10) and 400 (FIG. 12). In particular, the operations in FIG. 14 make it possible to produce apparatus in which an analyte-containing optical cavity occurs in a coating on top of a photosensing IC, allowing increased sensitivity and compactness of an optical sensor of analyte optical characteristics.

The operation in box 500 in FIG. 14 produces entry and exit partial optical cavity structures, with suitable parts to provide deformable spacers and electrodes for controlling cavity shape. This operation can include producing an entry light-reflective component, with or without a substrate such as an entry glass, and also producing an exit light-reflective component, again with or without a substrate such as an exit glass, with electrodes and deformable spacers fabricated photolithographically on one or both of the light-reflective components. Prior to fabricating the electrodes and spacers, this operation can include producing an entry light-reflective component on an entry glass (or directly on a light source such as an LED) and also producing an exit light-reflective component on an exit glass (or directly on a photosensitive surface, such as of a photosensing array or PSD). This operation can also include producing a patterned layer of a deformable material, e.g., an elastomer such as SU-8 or polydimethylsiloxane (PDMS) on one or both of the light-reflective components, such as with techniques described in co-pending U.S. patent application Ser. No. 11/315,992, entitled "Sensing Photons from Objects in Channels" and incorporated herein by reference in its entirety.

A patterned layer of elastomer or other deformable material could include structures that operate as spacers and walls, dimensioned and positioned to ensure that the resulting deformable components are capable of operating as desired, and with a desired degree of elasticity if appropriate. For example, a single piece of elastomer could be formed with a duct or channel running through it or with a well defined in one of its surfaces to receive analyte, or one set of elastomer parts could operate as spacers controlled by electrodes and another set could operate to bound ducts, channels, wells, or other bounded analyte regions.

In an alternative approach, electrodes and elastomer spacers could be fabricated on one of the light-reflective components and a second set of electrodes could be fabricated on top of the spacers; unless the second set of electrodes or other parts of the same layer also provide sufficient reflectivity, the other light-reflective component could then be placed on top of the second set of electrodes. In experimental implementations of this approach with a single elastomer spacer and silver mirror/electrodes, the first mirror/electrode has high reflectivity, but the second mirror/electrode has between approximately 60% and 80% reflectivity, apparently due to materials used and fabrication process; it is expected that a compromise can be reached by sacrificing voltage response to achieve higher reflectivity by using of Sylgard 182 elastomer with less or no oil, by using other elastomer materials, by using metal transfer processes for the second mirror/electrode or by making other changes in materials or processes.

The material used in box 500 to produce deformable components can be an elastomer, i.e. an elastic substance resembling rubber, or other deformable material chosen so that it responds appropriately to the operation that causes deformation, whether an electroactive, electrostatic, electromagnetic, magnetic, piezoelectric, mechanical, or other type of operation. If the material also has surfaces that bound and define ducts, channels, wells, or other regions to contain analyte, as suggested in FIG. 1, material can be chosen that is compatible with expected characteristics of analyte, including pH, viscosity, likely reactions with materials, and so forth. If appropriate, an anti-adhesive coating can be applied to interior duct, channel, or well surfaces, such as by dip-coating polyethylene glycol (PEG) or by providing a coating of parylene C or vapor deposited tetraglyme, and the choice of coating must also be compatible with the deformable material.

In another approach, the operation in box 500 can be implemented using an elastomer, gel, or oil between the mirrors in a silicon-based MEMS or piezoelectrically controlled tunable cavity to increase tuning range. In this case, the elastomer's electroactive property would not be used, but the elastomer would increase refractive index. If a liquid is used, the liquid and the movable mirror can be moved in various ways, such as by using PZT to produce a traveling wave in the liquid.

The operation in box 502 then attaches the entry and exit partial structures, with attached fluidic components to position analyte in the resulting optical cavity. The operation in box 502 can include forming a suitable bond between the entry and exit partial structures so that they are firmly attached to each other. Also, the fluidic components attached to the resulting optical cavity structure can include, for example, connectors, tubing, pumps, sensors, and so forth; it is important that the combination of fluidic components be capable of operating to cause and control positioning of analyte within the optical cavity, such as by carrying the analyte into the optical cavity with a fluid or in some other way. The operation in box 502 can also optionally include attachment of wires or other appropriate circuitry connected, for example, to the photosensing array.

The operation in box 504 then attaches any other additional components necessary to complete the device. For example, if the device includes light sources, these components can be attached by the operation in box 504. Similarly, if a photosensing array is not part of the exit partial structure, a photosensing component can be attached by the operation in box 504. The operation in box 504 can also include any other external electrical, optical, or fluidic connections necessary for operation of the device, including any necessary connections from external circuitry to electrodes to control elastomer, as shown. Alternatively, such connections could later be made when the device is incorporated into a system, such as system 200 in FIGS. 7 and 8.

The choice of a detector can be made based on several constraints. For example, if intensity peaks of a small number of modes are photosensed to detect changes in central energy or position, amplitude, contrast, and FWHM, it may be possible to use a respective one-dimensional photosensing array for each optical cavity, with each array including a relatively small number of cells, reducing the electrical power requirement because less power is dissipated in the detector. In general, compactness is promoted by using a photosensing IC, as described in co-pending U.S. patent application Ser. No. 11/702,250, entitled "Photosensing Optical Cavity Output Light" and incorporated by reference herein in its entirety.

The operation in box 506 can be performed at any appropriate time after the other operations, as suggested by the dashed line from box 504 to box 506. In addition, the operation in box 506 performs calibration, which requires that components be appropriately connected to circuitry, such as in the ways illustrated in FIGS. 7 and 8. The necessary connections could be created as part of the operations in boxes 500, 502, and 504 or instead could be created after the operation in box 504 and before performing calibration. In any case, calibration in box 506 can include obtaining items of data or data structures to be used in obtaining analyte information as described herein, and the data or data structures can be stored in memory 246 as part of calibration data 276 (FIG. 8), or, in appropriate cases, can be embedded in analyte information routine 274 or stored in another appropriate form.

A typical fabrication process that roughly follows boxes 500, 502, 504, and 506 and that should be simple and cheap and would allow fabrication as in FIG. 10 of an optical cavity structure directly on top of a photosensitive surface, such as of a photosensing array or a PSD, could proceed as follows: First, a dielectric or metal mirror (that may also include bottom electrodes) Is formed by deposition of material on a substrate or on top of the photosensitive surface; if a dielectric mirror is used or if otherwise necessary or desirable such as to separately optimize mirror and electrode performance, a conductive layer is then deposited and photolithographically patterned to form bottom electrodes for the spacers; an elastomer layer is then formed and patterned to form spacers, such as by spin casting and structuring PDMS on top of the bottom electrodes; top electrodes are then formed on top of the spacers, such as by depositing and photolithographically patterning another conductive layer; and then a second dielectric or metal mirror is attached over the top electrodes, stabilized if necessary by an appropriate substrate.

The typical fabrication process described above can be modified for various specific purposes. For example, the top and/or bottom electrode layers can be patterned photolithographically to provide individual addressing of electrodes. Also, a specific thickness of elastomer can be used that allows desired cavity thicknesses. After both sets of electrodes have been formed, they can be connected and spacers can be adjusted by tuning the cavity in situ during the fabrication process; for example, the cavity can be illuminated by a homogeneous, parallel narrow band light source and adjustment can be made to obtain a desired interference pattern in the output light, photosensed by a camera, After in situ tuning, cavity thickness can be fixed with glue or epoxy, potentially in combination with a spacer material exhibiting low thermal expansion coefficient, such as Zerodur. Before sealing the cavity completely, it may be advantageous to fill parts of the cavity that will not contain analyte with a high-index medium in order to minimize dependence of its characteristics on angle of incident light.

For a cavity that can be further tuned after fabrication is completed, a coarse fabrication can first be performed as described above, such as by tuning voltages across the spacers to get desired capacitances between measurement or control electrodes. After fabrication, a calibration operation as in box 506 could correlate voltage settings with optical properties. This approach could be employed both for a cavity on a substrate and for a cavity integrated on top of a photosensitive surface of a photosensing component.

In general, the operations in any of boxes 500, 502, 504, and 506 can include additional activities. For example, at any appropriate point in production of the device, wires or other appropriate circuitry can be attached to provide signals to or from a microprocessor or input/output (I/O) device to pumps and other fluidic components or to provide signals from a photosensing array to a microprocessor or I/O device. Similarly, connections can be made at any appropriate time to provide power.

The technique of FIG. 14 could be modified in many ways within the scope of the invention. For example, the operations in boxes 500, 502, and 504 could be combined in any appropriate way to facilitate attachment of components in a desired sequence. Also, an additional operation could be performed to align or attach interconnects between ICs, gates, and other circuitry, such as connectors to a microprocessor or computer, or this operation could be partially performed in each of boxes 500, 502, 504, and 506. Furthermore, the technique of FIG. 14 is extremely general, and could be employed to produce a wide variety of different devices that encode information about optical characteristics of analyte within an optical cavity and obtain sensing results indicating the optical characteristics. Examples described above show how objects can be carried through a channel within an optical cavity while such operations are performed, but various other arrangements are possible, some examples of which are described below.

Some of the implementations described above in relation to FIGS. 1-14 illustrate examples of devices that include a tunable optical cavity structure with a light-transmissive region between two inward reflection surfaces. Its optical cavity operation can be tuned by relative movement between the reflection surfaces. The structure can include an analyte region that can contain analyte within the light-transmissive region. Presence of the analyte in the analyte region affects the optical cavity's output light when it is tuned to a set of relative positions of the reflection surfaces. The optical cavity structure also includes a tuning structure that can tune it to at least one of the set of relative positions.

In specific implementations, the optical cavity structure can include two light-reflective components that include the reflection surfaces, and deformable components connected to move the light-reflective components, moving the reflection surfaces between relative positions in the set. Each deformable component can be elastically deformable.

In further specific implementations, the set of relative positions can include a range of continuously varying relative positions, and the tuning structure can tune the optical cavity continuously across the range. For example, if the optical cavity provides analyte-affected output light while the tuning structures tunes it continuously across the range, the output light can indicate continuous values of an optical characteristic of the analyte across a range of photon energies. The optical characteristic can be refractive index or absorption coefficient, for example.

Some of the implementations described above in relation to FIGS. 1-14 also illustrate examples of a system that includes an optical cavity device as described above, a photosensing component, and control circuitry. In response to control signals, the photosensing component can photosense the optical cavity's output light and provide sensing results with a readout frequency. The tuning structure can tune the optical cavity by changing the relative positions of the reflection surfaces at a tuning frequency. The control circuitry can provide tuning signals to the tuning structure and control signals to the photosensing component to lock in the tuning frequency and the readout frequency.

Some of the implementations described above in relation to FIGS. 1-14 also illustrate examples of methods that include tuning and optical cavity structure as described above. The act of tuning the optical cavity structure can include tuning it continuously across a range of relative positions.

In specific implementations, the analyte can be fluidically carried into the analyte region using a liquid, a gas, or an aerosol.

Some of the implementations described above in relation to FIGS. 1-14 also illustrate examples of methods that produce an optical cavity device and a tuning structure. The act of producing the optical cavity device can include producing the optical cavity structure with an analyte region as described above.

Some of the implementations described above in relation to FIGS. 1-14 also illustrate examples of optical cavity devices that include two light-reflective components with a light-transmissive region between them into which they are able to reflect light. The devices also include a tuning structure that, in response to tuning signals, can move the light-reflective components to any of a set of positions relative to each other.

The tuning structure includes deformable components as described above and at least one signal-responsive component that receives the tuning signals and, in response, causes deformation of at least one of the deformable components. The light-transmissive region can include an analyte region capable of having analyte in it, and the set of positions of the reflective components includes a subset in which the device operates as an optical cavity, providing analyte-affected output light that includes information about optical characteristics of the analyte.

In specific implementations, each deformable unit can be elastically deformable. The analyte region can be defined in one of the deformable components. The optical cavity can be a Fabry-Perot cavity. The light-reflective components can be layered structures with alternating layers at which light is reflected. Also, their facing surfaces can have reflective coatings on them.

In further specific implementations, the deformable component can include elastomer spacers between the light-reflective components. The elastomer spacers can include poly-di-methyl-siloxane, or, more generally, an electroactive elastomer material. The analyte region can be bounded by elastomer spacers. The analyte region can be a channel through which analyte is fluidically carried.

In further specific implementations, the tuning structure can include sensing components that provide shape sense signals indicating shape of the deformable components. The signal-responsive components can include electrodes connected to opposite surfaces of the deformable components. The analyte-affected output light can have a laterally varying intensity distribution. The device can also include a photosensing component, and the optical cavity's exit surface can be on or over the photosensing component's photosensitive surface.

Some of the implementations described above in relation to FIGS. 1-14 also illustrate examples of systems that include optical cavity devices as described above and control circuitry. The control circuitry can provide the tuning signals to the signal-responsive component.

In specific implementations, the system can also include sensing components that provide shape sense signals indicating shape of the deformable components, and the control circuitry can receive the shape sense signals and provide the tuning signals based on them. The signal-responsive components can include electrodes connected to opposite surfaces of the deformable components, and the control circuitry can measure capacitance between the electrodes to sense the deformable component's shape. A method of operating the system can include operating the control circuitry to provide a series of tuning signals so that the tuning structure moves the reflective components continuously across a range of relative positions within the set.

Some of the implementations described above in relation to FIGS. 1-14 also illustrate examples of methods of producing an optical cavity device as described above. The act of producing the optical cavity device can include producing it with an analyte region as described above.

In specific implementations, the act of producing the optical cavity device can also include depositing and patterning a layer of elastomer to produce the deformable components, and the elastomer can, for example, be poly-dio-methyl-siloxane.

In further specific implementations, the method can include producing an underlying structure that includes one light-reflective component on a photosensitive surface of a photosensing component, then performing the act of depositing and patterning, and then attaching an overlying structure over the deformable components, with the overlying structure including the other light-reflective components. Also, electrodes can be produced on an upper surface of the underlying structure before depositing and patterning the elastomer material, and other electrodes can be produced on the upper surfaces of the deformable components before attaching the overlying structure.

In further specific implementations, a sequence of tuning signals can be provided to the signal-responsive component to cause the deformable components to be deformed into a sequence of shapes. During the sequence of tuning signals, when output light from the optical cavity meets a criterion, the deformable components' shapes can be fixed.

The implementations in FIGS. 1-14 illustrate various applications of techniques as described above, including production and use of various analyte-containing homogeneous and inhomogeneous optical cavity devices with adjustable spectral range and, for LVFs, adjustable gradient, with the adjustments depending on the application and available both during production and use. Such devices can be combined with photosensing components that photosense output light from modes of tunable optical cavities that contain analyte and obtaining information about the analyte, such as about its refractive index and absorption coefficient. The techniques could be readily extended to obtain information about polarization and fluorescence. More generally, tunable analyte-containing optical cavities, such as Fabry-Perot interferometers or etalons, could be used to selectively filter narrow wavelength bands from incident broadband radiation in accordance with analyte optical characteristics; in combination with a detector, such as one that includes a photosensor array, a tunable optical cavity can be used as a spectrometer. In general, tunable optical cavities as described above are suitable for integration with other devices, such as semiconductor devices, making them appropriate for a wide variety of other applications, such as with individually addressable arrays of Fabry-Perot cavities.

Techniques that obtain information about analytes, as exemplified by the implementations in FIGS. 1-14, can be applied in many measuring techniques. For example, fluidic sensing, e.g. liquid, gas, or aerosol, could be performed with infrared illumination. For these applications, a tunable optical cavity with features similar to commercially available LVFs in the visible range might be appropriate. Especially interesting spectral ranges for gas sensing include 8 μm to 14 μm with 600 nm/mm gradient, and with the mirror spaced at 12-20 μm over 1 cm for a $3\lambda/2$ cavity and 3 μm to 5 μm with 200 nm/mm gradient, and with the mirror spaced at 4.5-7.5 μm over 1 cm for a $3\lambda/2$ cavity. Other interesting ranges for sensing applications include the mid-infrared (2-5 μm) and long wave infrared (6-12 μm).

Another potential area of application is in distinguishing objects such as biological cells, such as by counting, sorting, and so forth. Using a reference medium with no cells or objects in a device can eliminate the influence of varying environmental changes, as described in co-pending U.S. patent application Ser. No. 11/702,329, entitled "Implanting Optical Cavity Structures" and incorporated herein by reference in its entirety. Related techniques could be used to obtain probability of a certain type of object, such as cancerous cells. Also, for rare cell scanning, the above techniques may be useful because they can provide high throughput (counting/sorting speed): if a high number of parallel channels can be used, e.g. 200, it may be possible to sort 1 out of 10,000,000 cells within a few seconds using a device with the typical dimensions of a CMOS detector chip. Techniques for distinguishing objects are described in greater detail in co-pending U.S. patent application Ser. No. 11/702,249, entitled "Distinguishing Objects" and incorporated herein by reference in its entirety.

Another potential area of application is in implantable products useful to obtain information about analytes such as glucose in bodily fluids, as also described in co-pending U.S. patent application Ser. No. 11/702,329, referenced above. Since typical dimensions of a device as described are in the 3-12 µm range, such devices should be able to handle high water background absorption in the 3 µm as well as the 8-12 µm range.

Various of the techniques described above have been successfully implemented or simulated, including the production and operation of chip-size detectors that include LVFs on photosensing ICs. The influence of an analyte in the cavity of an etalon has been experimentally tested and simulated. Prototypes of elastomer-based devices with deformations up to 200 nm, approximately 4% of elastomer thickness, have been demonstrated, and it appears that further scaling is feasible using thicker or thinner films. In particular, elastically deformable spacers with small lateral dimensions are expected to allow for larger tuning ranges.

The exemplary implementations described above allow compact, inexpensive components to rapidly and accurately perform operations such as measuring optical characteristics of fluids, biological cells, glucose, and other analytes. In particular, such implementations make it possible to use deformable components that operate both to change optical cavity characteristics, such as by changing thickness and tilt, and also to bound, contain, or otherwise define regions within the cavity that can contain analyte. This approach provides greater flexibility than previous techniques to control optical cavity thickness, such as with piezoelectric or MEMS components. At the same time, the techniques described above could be implemented in combination with piezoelectric or MEMS components; for example, deformable components such as spacers could be made from thin film piezoelectric material.

A wide range of implementations is available with techniques described above, making it possible to overcome problems with previous approaches to tunable optical cavities. Compared to proposed techniques that change refractive index of electro-optic material in a cavity, it is possible to operate devices as described above with lower voltages and larger tuning ranges. Also, thin film manufacturing techniques as described above are generally less complex and more reliable, cost effective, and robust, especially compared with the power and thermal requirements and labor intensive aspects of piezoelectric device production and with the complex, expensive, and low-yield surface or bulk micromachining operations used in for silicon MEMS-based approaches. Such manufacturing difficulties tend to increase for parallel plate structures due to the tight tolerances on parallel orientation, on the order of tens of nanometers for high performance.

The exemplary implementations described above employ optical cavities with specific parameters and modes, but a wide variety of cavities could be used. Cavities with widths in the range from a few µm to hundreds of µm are feasible, and photon energies ranging from the ultraviolet up to the far infrared could be sampled.

In addition, components could have various shapes, dimensions, or other numerical or qualitative characteristics other than those illustrated and described above. For example, in some exemplary implementations described above, cells of a photosensor array photosense in different subranges of an application's photon energy range. The subranges of cells could have any appropriate widths and relationships, and could, for example, overlap or be distinct. The width of a cell's subrange can be chosen by designing an optical cavity and the cell sensing area; for example, the width may be as small as 0.1 nm or as great as tens of nanometers.

Some of the above exemplary implementations involve specific materials, such as in deformable components such as spacers, in signal-responsive components such as electrodes, in photosensor arrays or position-sensitive detectors, and in components that provide optical cavities such as mirrors, but the invention could be implemented with a wide variety of materials and with layered structures with various combinations of sublayers. In particular, photosensor arrays for a desired speed, sensitivity and wavelength range could have any suitable material, such as silicon, germanium, indium-gallium-arsenide, gallium arsenide, gallium nitride, or lead sulphide, and could be produced with any appropriate kind of devices, including, for example, photodiodes, avalanche photodiodes, p-i-n diodes, photoconductors, and so forth, with any appropriate technique for sensing and reading out information whether based on CCD, CMOS, or other techniques. Various commercially available detector arrays have pixel densities as high as ten megapixels, and some high density ICs have become relatively inexpensive.

Similarly, optical cavities and related components could be fabricated with any appropriate techniques, including thin film technology such as sputtering, e-beam or thermal evaporation with or without plasma assistance, epitaxial growth, MBE, MOCVD, and so forth. To produce Bragg mirrors, appropriate pairs of materials with low absorption coefficients and large difference in refractive indices could be chosen, bearing in mind the photon energies of interest; exemplary materials include $SiO_2/TiO_2$, $SiO_2/Ta_2O_5$, GaAs/AlAs, and GaAs/AlGaAs. Thicknesses of layer in optical cavities may vary from 30 nm up to a few hundred nanometers.

Some of the above exemplary implementations could involve particular types of optical cavity structures, such as Bragg mirrors and paired distributed Bragg reflectors separated by a Fabry-Perot cavity, but, more generally, any appropriate optical cavity structure could be used to produce a laterally varying energy distribution, including a homogeneous optical cavity illuminated across a range of angles of incidence by a point light source.

Some of the above exemplary implementations use specific lasers or other light sources to obtain light with desired characteristics, but various other light source techniques could be used within the scope of the invention. Various propagation components that propagate light between other components could also be employed.

The exemplary implementation in FIGS. 8 and 9 employs a CPU, which could be a microprocessor or any other appropriate component. Furthermore, as noted above, adjustment, combining, and other operations on photosensed quantities could be done either digitally or with analog signals, and could be done either on the same IC as a photosensor array, on other components, or on a combination of the two, with any appropriate combination of software or hardware.

The above exemplary implementations generally involve production and/or use of ICs and other photosensing components, optical cavities, elastically deformable components such as spacers, signal-responsive components such as electrodes, light sources, processing circuitry, and control circuitry following particular operations, but different operations could be performed, the order of the operations could be modified, and additional operations could be added within the scope of the invention. For example, readout of adjusted or unadjusted photosensed quantities from an IC could be performed serially or in parallel, and could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. An optical cavity device comprising:
   first and second light-reflective components with a light-transmissive region between them, each of the light-reflective components being structured to reflect light into the light-transmissive region;
   a tuning structure that is structured to respond to tuning signals by moving the first and second light-reflective components among a set of positions relative to each other; the tuning structure including:
      one or more deformable components connected so that deformation of at least one of the deformable components causes the first and second light-reflective components to move within the set of positions; and
      at least one signal-responsive component that receives the tuning signals and, in response, causes deformation of at least one of the deformable components;
   the light-transmissive region including an analyte region, the analyte region being bounded in part by at least one of the deformable components; and
   a fluidic component that, in operation, provides an analyte in the analyte region;
   the set of positions including a subset of one or more positions in which the first and second light-reflective components and the light-transmissive region with analyte from the fluidic component in the analyte region are configured to operate as an optical cavity that provides analyte-affected output light, the analyte-affected output light including information about one or more optical characteristics of the analyte.

2. The device of claim 1, further comprising:
   control circuitry that provides tuning signals that cause the tuning structure to change relative positions of the first and second light-reflective components at a tuning frequency.

3. A system comprising the device of claim 2, further comprising:
   a photosensing component that, in response to control signals, photosenses the optical cavity's output light and provides sensing results with a readout frequency;
   the control circuitry further providing control signals to the photosensing component, the tuning signals and the control signals locking in the tuning frequency and the readout frequency.

4. The device of claim 1 in which the first and second light-reflective components include the first and second reflection surfaces, respectively; in moving the first and second light-reflective components, the tuning structure moving the first and second reflection surfaces relative to each other.

5. The device of claim 1 in which the set of positions includes a range of continuously varying relative positions; the tuning structure being structured to change relative positions of the first and second light-reflective components continuously across the range.

6. The device of claim 5 in which the optical cavity provides analyte-affected output light while the tuning structure changes relative positions of the first and second light-reflective components continuously across the range, the output light indicating continuous values of an optical characteristic of the analyte across a range of photon energies.

7. The device of claim 6 in which the optical characteristic is one of refractive index and absorption coefficient.

8. The device of claim 1 in which each deformable component is elastically deformable.

9. The device of claim 1 in which the analyte region is defined in one of the deformable components.

10. The device of claim 1 in which the first and second light-reflective components include first and second facing surfaces, respectively, the first and second facing surfaces each having a respective reflective coating.

11. The device of claim 1 in which the one or more deformable components include one or more elastomer spacers between the first and second light-reflective components.

12. The device of claim 11 in which the elastomer spacers include poly-di-methyl-siloxane.

13. The device of claim 11 in which the elastomer spacers include electroactive elastomer material.

14. The device of claim 11 in which the analyte region is bounded by the elastomer spacers.

15. The device of claim 1 in which the analyte region is a channel; the fluidic component causing the analyte to be fluidically carried through the channel.

16. The device of claim 1 in which the tuning structure further includes:
   one or more sensing components structured to provide shape sense signals indicating shape of one of the deformable components.

17. The device of claim 1 in which the signal-responsive components include:
   first and second electrodes connected to opposite surfaces of one of the deformable components.

18. The device of claim 1 in which the analyte-affected output light has a laterally varying intensity distribution.

19. The device of claim 1 in which the optical cavity provides output light at an exit surface, the device further comprising:
   a photosensing component with a photosensitive surface; the exit surface being on or over the photosensitive surface.

20. A system comprising the device of claim 1, the system further comprising:
   control circuitry connected to the signal-responsive component, the control circuitry providing the tuning signals.

21. The system of claim 20 in which the tuning structure further includes:
   one or more sensing components structured to provide shape sense signals indicating shape of one or more of the deformable components; the control circuitry receiving the shape sense signals and providing the tuning signals based on the shape sense signals.

22. The system of claim 21 in which the sensing components include:
   first and second electrodes connected to opposite surfaces of the deformable component; the control circuitry measuring capacitance between the first and second electrodes to sense the deformable component's shape.

23. An optical cavity device comprising:
   first and second structures that include first and second light-reflective components, respectively;
   between the first and second light-reflective components, an in homogeneous optical cavity; each of the light-reflective components being structured to reflect light into the inhomogeneous optical cavity;

connected to the first and second structures, a set of one or more tuning structures that are structured to move the first and second structures among a set of positions relative to each other; at least one of the tuning structures in the set including:

first and second electrodes connected to the first and second structures, respectively, the first and second electrodes being connectible to receive electrical tuning signals; and a respective deformable component between the first and second electrodes; the deformable component being deformable in response to the electrical tuning signals received by the first and second electrodes the deformable component being connected so that deformation of the deformable component causes the first and second structures to move within the set of positions;

an analyte region within the inhomogeneous optical cavity, the analyte region being bounded in part by the respective deformable component of at least one of the tuning structures; and a fluidic component that, in operation, provides an analyte in the analyte region;

the optical cavity device being structured so that, in a subset of one or more positions in the set of positions, presence of the analyte in the analyte region affects the inhomogeneous optical cavity's output light and the output light includes information about one or more optical characteristics of the analyte.

24. The device of claim 23 in which the first and second electrodes of each tuning structure in the set are on facing surfaces of the first and second structures, respectively.

25. The device of claim 23 in which the deformable component includes at least one of:

dielectric elastomer material that is deformed in response to an electrostatic field between electrodes;

nonmagnetic elastomer material that is deformed by electromagnetic attraction or repulsion between electrodes; and piezoelectric material that expands or contracts in response to electrical signals received through electrodes.

26. The device of claim 23 in which the set of tuning structures, by moving the first and second structures, changes the optical cavity's shape by doing at least one of changing a tilt angle and changing an optical distance.

27. The device of claim 23 in which the optical cavity device has an exit surface at which it provides the in homogeneous optical cavity's output light, the device further comprising:

a photosensing component connected to the exit surface to receive the output light.

28. A system that comprises the device of claim 23, the system further comprising:

one or more sensing components structured to sense a feature of relative position of the first and second light-reflective components and provide feature signals indicating the sensed feature; and control circuitry connected to receive the feature signals; in response to the feature signals, the control circuitry providing the electrical tuning signals to the set of tuning structures.

29. The system of claim 28 in which the control circuitry comprises a processor, the processor providing the electrical tuning signals based on the feature signals and on calibration data.

30. The system of claim 28 in which the sensing components sense distance between the first and second light-reflective components.

\* \* \* \* \*